US007419784B2

(12) United States Patent
Dubrow et al.

(10) Patent No.: US 7,419,784 B2
(45) Date of Patent: Sep. 2, 2008

(54) METHODS, SYSTEMS AND APPARATUS FOR SEPARATION AND ISOLATION OF ONE OR MORE SAMPLE COMPONENTS OF A SAMPLE BIOLOGICAL MATERIAL

(76) Inventors: Robert S. Dubrow, 766 Orange Ave., San Carlos, CA (US) 94070; Luc J. Bousse, 1050 Rilma La., Los Altos, CA (US) 94022; Huan L. Phan, 1512 Chula Vista Dr., Belmont, CA (US) 94002

( * ) Notice: Subject to any disclaimer, the term of this patent is extended or adjusted under 35 U.S.C. 154(b) by 529 days.

(21) Appl. No.: 10/401,110

(22) Filed: Mar. 27, 2003

(65) Prior Publication Data

US 2003/0215855 A1 Nov. 20, 2003

Related U.S. Application Data

(60) Provisional application No. 60/369,371, filed on Apr. 2, 2002.

(51) Int. Cl.
*G01N 33/53* (2006.01)
(52) U.S. Cl. ............................ 435/6; 435/7.1; 436/514; 436/174; 422/50
(58) Field of Classification Search ......... 204/600–601, 204/450–451; 435/91.2, 6, 7.1, 9
See application file for complete search history.

(56) References Cited

U.S. PATENT DOCUMENTS

| | | | |
|---|---|---|---|
| 4,390,403 A | 6/1983 | Batchelder | |
| 4,711,955 A | 12/1987 | Ward et al. | |
| 4,908,112 A | 3/1990 | Pace | |
| 5,126,022 A | 6/1992 | Soane et al. | |
| 5,171,534 A | 12/1992 | Smith et al. | |
| 5,187,085 A | 2/1993 | Lee | |
| 5,188,934 A | 2/1993 | Menchen et al. | |
| 5,366,860 A | 11/1994 | Bergot et al. | |

(Continued)

FOREIGN PATENT DOCUMENTS

WO    WO-9604547    2/1996

(Continued)

OTHER PUBLICATIONS

Gottschlich, N. et al., "Two-Dimensional Electrochromatography/Capillary Electrophoresis on a Microchip," Anal. Chem. (2001) 73:2669-2674.

(Continued)

*Primary Examiner*—Nelson Yang
(74) *Attorney, Agent, or Firm*—Cardinal Law Group

(57) ABSTRACT

Devices, systems and methods for use in separating sample materials into different sample components and then isolating one or more of the sample components for further processing or analysis are disclosed. Devices employ configurations that optionally allow a sample material to be electrophoretically separated into sample components in a separation matrix within a separation conduit. The sample components may then be detected in a detection zone in the separation conduit, and then selected components shunted to a component collection conduit within the device downstream of the detection zone for further processing or analysis based on information received at the detection zone. Methods of using these devices, and systems that incorporate these devices are also envisioned.

31 Claims, 7 Drawing Sheets

U.S. PATENT DOCUMENTS

| | | | |
|---|---|---|---|
| 5,498,392 | A | 3/1996 | Wilding et al. |
| 5,571,410 | A | 11/1996 | Swedberg et al. |
| 5,585,069 | A | 12/1996 | Zanzucchi et al. |
| 5,593,838 | A | 1/1997 | Zanzucchi et al. |
| 5,603,351 | A | 2/1997 | Cherukuri et al. |
| 5,635,358 | A | 6/1997 | Wilding et al. |
| 5,637,469 | A | 6/1997 | Wilding et al. |
| 5,699,157 | A | 12/1997 | Parce |
| 5,716,852 | A | 2/1998 | Yager et al. |
| 5,750,015 | A | 5/1998 | Soane et al. |
| 5,779,868 | A | 7/1998 | Parce et al. |
| 5,800,690 | A | 9/1998 | Chow et al. |
| 5,858,187 | A | 1/1999 | Ramsey et al. |
| 5,858,195 | A | 1/1999 | Ramsey |
| 5,869,004 | A | 2/1999 | Parce et al. |
| 5,876,675 | A | 3/1999 | Kennedy |
| 5,880,071 | A | 3/1999 | Parce et al. |
| 5,882,465 | A | 3/1999 | McReynolds |
| 5,885,470 | A | 3/1999 | Parce et al. |
| 5,932,100 | A | 8/1999 | Yager et al. |
| 5,942,443 | A | 8/1999 | Parce et al. |
| 5,948,227 | A | 9/1999 | Dubrow |
| 5,955,028 | A | 9/1999 | Chow |
| 5,958,694 | A | 9/1999 | Nikiforov |
| 5,959,291 | A | 9/1999 | Jensen |
| 5,965,410 | A | 10/1999 | Chow et al. |
| 5,976,336 | A | 11/1999 | Dubrow et al. |
| 5,989,402 | A | 11/1999 | Chow et al. |
| 6,001,229 | A | 12/1999 | Ramsey |
| 6,001,231 | A | 12/1999 | Kopf-Sill |
| 6,012,902 | A | 1/2000 | Parce |
| 6,042,709 | A | 3/2000 | Parce et al. |
| 6,043,080 | A | 3/2000 | Lipshutz et al. |
| 6,046,056 | A | 4/2000 | Parce et al. |
| 6,062,261 | A | 5/2000 | Jacobson et al. |
| 6,071,478 | A | 6/2000 | Chow |
| 6,074,725 | A | 6/2000 | Kennedy |
| 6,100,541 | A | 8/2000 | Nagle et al. |
| 6,120,666 | A | 9/2000 | Jacobson et al. |
| 6,150,119 | A | 11/2000 | Kopf-Sill et al. |
| 6,221,226 | B1 | 4/2001 | Kopf-Sill |
| 6,221,654 | B1 | 4/2001 | Quake et al. |
| 6,235,471 | B1 | 5/2001 | Knapp et al. |
| 6,238,538 | B1 | 5/2001 | Parce et al. |
| 6,264,825 | B1 | 7/2001 | Blackburn et al. |
| 6,280,589 | B1 | 8/2001 | Manz et al. |
| 6,294,063 | B1 | 9/2001 | Becker et al. |
| 6,344,325 | B1 | 2/2002 | Quake et al. |
| 6,344,326 | B1 | 2/2002 | Nelson et al. |
| 6,406,893 | B1 * | 6/2002 | Knapp et al. ............... 435/91.2 |
| 6,416,642 | B1 | 7/2002 | Alajoki et al. |
| 6,444,461 | B1 | 9/2002 | Knapp et al. |
| 6,475,364 | B1 | 11/2002 | Dubrow et al. |
| 6,485,625 | B1 * | 11/2002 | Simpson et al. ............. 204/601 |
| 6,540,895 | B1 | 4/2003 | Spence et al. |
| 2002/0019059 | A1 | 2/2002 | Chow et al. |
| 2002/0127736 | A1 * | 9/2002 | Chou et al. ................. 436/180 |

FOREIGN PATENT DOCUMENTS

| | | |
|---|---|---|
| WO | WO-9702357 | 1/1997 |

OTHER PUBLICATIONS

Dasgupta, P.K. et al., "Electroosmosis: A Reliable Fluid Propulsion System for Flow Injection Analysis," *Anal. Chem.* (1994) 66:1792-1798.

Effenhauser, C.S. et al., "Glass Chips for High-Speed Capillary Electrophoresis Separations with Submicrometer Plate Heights," *Anal. Chem.* (1993) 65: 2637-2642.

Effenhauser, C.S. et al., "High Speed Separation of Anitsense Oligonucleotides on a Micromachined Capillary Electrophoresis Device," *Anal. Chem.* (1994) 66: 2949-2953.

Effenhauser, C.S. et al., "Integrated Capillary Electrophoresis on Flexible Silicone Microdevices: Analysis of DNA Restriction Fragments and Detection of Single DNA Molecules on Microchips," *Anal. Chem.* (1997) 69: 3451-3457.

Fan, Z.H. et al., "Micromachining of Capillary Electrophoresis Injectors and Separators on Glass Chips and Evaluation of Flow at Capillary Intersections," *Anal. Chem.* (1994) 66: 177-184.

Fister, J.C. III et al., "Counting Single Chromophore Molecules for Ultrasensitive Analysis and Separations on Microchip Devices," *Anal. Chem.* (1998) 70: 431-437.

Hadd, A.G. et al., "Microfluidic Assays of Acetylcholinesterase," *Anal. Chem.* (1999) 71: 5206-5212.

Harrison, J. et al., "Capillary Electrophoresis and Sample Injection Systems Integrated on a Planar Glass Chip," *Anal. Chem.* (1992) 64: 1926-1932.

Harrison, J. et al., "Towards Miniaturized Electrophoresis and Chemical Analysis Systems on Silicon: An Alternative to Chemical Sensors," *Sensors and Actuators B* (1993) 10: 107-116.

Harrison, J. et al., "Micromachining a Miniaturized Capillary Electrophoresis-Based Chemical Analysis System on a Chip," *Science* (1993) 261: 895-897.

Harrison, D.J. et al., "Integrated Electrophoresis Systems for Biochemical Analyses," *Solid-State Sensor and Actuator Workshop* (1994) 21-24.

Jacobson, S.C. et al., "Effects of Injection Schemes and Column Geometry on the Performance of Microchip Electrophoresis Devices," *Anal. Chem.* (1994) 66:1107-1113.

Jacobson, S.C. et al., "High-Speed Separations on a Microchip," *Anal. Chem.* (1994) 66: 1114-1118.

Jacobson, S.C. et al., "Open Channel Electrochromatography on a Microchip," *Anal. Chem.* (1994) 66: 2369-2373.

Jacobson, S.C. et al., "Precolumn Reactions with Electrophoretic Analysis Integrated on a Microchip," *Anal. Chem.* (1994) 66: 4127-4132.

Jacobson, S.C. et al., "Microchip Electrophoresis with Sample Stacking," *Electrophoresis* (1995) 16: 481-486.

Jacobson, S.C. et al., "Fused Quartz Substrates for Microchip Electrophoresis," *Anal. Chem.* (1995) 67: 2059-2063.

Jacobson, S.C. et al., "Integrated Microdevice for DNA Restriction Fragment Analysis," *Anal. Chem.* (1996) 68: 720-723.

Jacobson, S.C. et al., "Electrokinetic Focusing in Microfabricated Channel Structures," *Anal. Chem.* (1997) 69: 3212-3217.

Jacobson, S.C. et al., "Microfluidic Devices for Electrokinetically Driven Parallel and Serial Mixing," *Anal. Chem.* (1999) 71: 4455-4459.

Manz, A. et al., "Miniaturized Total Chemical Analysis Systems: a Novel Concept for Chemical Sensing," *Sensors and Actuators* (1990) B1: 244-248.

Manz, A. et al., "Micromachining of Monocrystalline Silicon and Glass for Chemical Analysis Systems," *Trends in Analytical Chemisty* (1991) 10:144-149.

Manz, A. et al., "Planar Chips Technology for Miniaturization and Integration of Separation Techniques into Monitoring Systems," *Journal of Chromatography* (1992) 593:253-258.

Manz, A. et al., "Planar Chips Technology for Miniaturization of Separation Systems: A Developing Perspective in Chemical Monitoring,".

Manz, A. et al., "Electroosmotic Pumping and Electrophoretic Separations for Miniaturized Chemical Analysis Systems," *J. Micromach. Microeng.* (1994) 4: 257-265.

Manz, A. et al., "Parallel Capillaries for High Throughput in Electrophoretic Separations and Electroosmotic Drug Discovery Systems," International Conference on Solid-State Sensors and Actuators (1997) 915-918.

McCormick, R.M. et al., "Microchannel Electrophoretic Separations of DNA in Injection-Molded Plastic Substrates," *Anal. Chem.* (1997) 69: 2626-2630.

Moore, A.W. et al., "Microchip Separations of Neutral Species via Micellar Electrokinetic Capillary Chromatography," *Anal. Chem.* (1995) 67: 4184-4189.

Ramsey, J.M. et al., "Microfabricated Chemical Measurement Systems," *Nature Medicine* (1995) 1:1093-1096.

Salimi-Moosavi, H. et al., "Biology Lab-on-a-Chip for Drug Screening," Solid-State Sensor and Actuator Workshop (1998) 350-353.

Seiler, K. et al., "Planar Glass Chips for Capillary Electrophoresis: Repetitive Sample Injection, Quantitation, and Separation Efficiency," *Anal. Chem.* (1993) 65:1481-1488.

Seiler, K. et al., "Electroosmotic Pumping and Valveless Control of Fluid Flow within a Manifold of Capillaries on a Glass Chip," *Anal. Chem.* (1994) 66:3485-3491.

UEDA, M. et al., "Imaging of a Band for DNA Fragment Migrating in Microchannel on Integrated Microchip," *Materials Science and Engineering C* (2000) 12:33-36.

Wang, C. et al., "Integration of Immobilized Trypsin Bead Beds for Protein Degestion within a Microfluidic Chip Incorporating Capillary Electrophoresis Separations and an Electrospray Mass Spectrometry Interface," *Rapid Commin. Mass Spectrom.* (2000) 14:1377-1383.

Woolley, A.T. et al., "Ultra-High-Speed DNA Fragment Separations Using Microfabricated Capillary Array Electrophoresis Chips," *Proc. Natl. Acad. Sci. USA* (1994) 91:11348-11352.

Woolley, A.T. et al., "Functional Integration of PCR Amplification and Capillary Electrophoresis in a Microfabricated DNA Analysis Device," Anal. Chem. (1996) 68: 4081-4086.

Woolley, A.T. et al., "High-Speed DNA Genotyping Using Microfabricated Capillary Array Electrophoresis Chips," *Anal. Chem.* (1997) 69:2181-2186.

Woolley, A.T. et al., "Capillary Electrophoresis Chips with Integrated Electrochemical Detection," *Anal. Chem.* (1998) 70: 684-688.

Zhang, B. et al., "Microfabricated Devices for Capillary Electrophoresis-Electrospray Mass Spectrometry," *Anal. Chem.* (1999) 71:3258-3264.

\* cited by examiner

METHODS, SYSTEMS AND APPARATUS FOR SEPARATION AND ISOLATION OF ONE OR MORE SAMPLE COMPONENTS OF A SAMPLE BIOLOGICAL MATERIAL

CROSS-REFERENCE TO RELATED APPLICATION

This application claims the benefit of U.S. Provisional Patent Application No. 60/369,371, filed Apr. 2, 2002, which is incorporated herein by reference in its entirety for all purposes.

BACKGROUND OF THE INVENTION

Separations based analyses are a prominent part of biological research, allowing one to characterize different biological samples, reaction products and the like. Examples of some of the more prevalent separations based analyses include electrophoretic separations of macromolecular species, e.g., proteins and nucleic acids. Capillary electrophoresis has been established as a highly effective method for separating macromolecular species in order that they might be further characterized. Protein and nucleic acid molecules are two major examples of molecular species that are routinely fractionated and characterized using capillary electrophoretic systems. These systems have generally proven effective as a result of the high surface to volume ratio of the thin capillaries. This high surface to volume ratio allows for much greater heat dissipation, which in turn, allows application of greater electrical fields to the capillary thereby resulting in a much more rapid separation of macromolecules introduced into the system.

Microfluidic devices have been applied in separations based analyses, and have yielded substantial advantages in speed and accuracy. Examples of novel microfluidic devices and methods for use in the separation of molecular, and particularly macromolecular species by electrophoretic means are described in U.S. Pat. Nos. 5,958,694 and 6,032,710, for example, the entire contents of which are incorporated by reference herein. In such devices, the sample containing the macromolecular species for which separation is desired, is placed in one end of a separation channel located in the microfluidic substrate and a voltage gradient is applied along the length of the channel. As the sample components are electrophoretically transported along the length of the channel and through the separation (sieving) matrix disposed therein, those components are resolved. The separated components are then detected at a detection point along the length of the channel, typically near the terminus of the separation channel downstream from the point at which the sample was introduced. Following detection, the separated components are typically directed to a collection reservoir/well in the device (or to an external device such as a multiwell plate via a capillary pipettor, for example) for subsequent extraction or disposal.

In many situations, it is desirable to extract selected fragments of interest following the separation of the fragments into bands in the separation matrix, such as DNA fragments for further processing or analysis, e.g., restriction enzyme modification, T4 ligation, PCR amplification, mass spectroscopy, or polynucleotide kinase reactions. The typical process used by laboratory researchers for extracting and isolating selected DNA fragments of interest (and other desired nucleic acid and protein fragments) from a separation matrix (such as agarose gels) involves manually transferring the DNA fragments to a suitable transfer medium, where the separated fragments are stained and illuminated by shining ultraviolet (UV) light on the fragments to visualize the separated bands. A razor blade is then used to manually cut above and below each fragment of interest. The recovered DNA can then be used for further processing or analysis. Such extraction process, however, is time consuming, laborious and potentially damaging to the DNA (e.g., nicking of the DNA can occur if the DNA is exposed to ultraviolet light too long while the fragments of interest are being illuminated for excision).

Thus, in performing separations based analyses in microfluidic devices, for example, it would be desirable to not only be able to rapidly collect data regarding the relative size and/or molecular weights (based on comparisons to standards, for example) of the separated components, but it would also be desirable to be able to isolate or extract one or more of the separated components in the device itself for further analysis or processing in the device, since the microscale dimensions of the device offer advantages in terms of automation, speed, reduced consumption of expensive reagents (typically on the order of nanoliters), and more efficient use of manpower as well as increased throughput. The recovered or isolated fragments could then be used for a variety of different processes in the device including, for example, ligation reactions for cloning small to medium-sized strands of DNA into bacterial plasmids, bacteriophages, and small animal viruses to allow the production of pure DNA in sufficient quantities to allow its chemical analysis, reactions to dissolve a separated protein or nucleic acid component in a suitable matrix for further analysis by a mass spectrometer using, for example, Matrix-Assisted Laser Desorption Ionization (MALDI), binding reactions to bind a labeling agent to one or more separated protein or nucleic acid components for further analysis, or other similar post-detection processes. In addition, in the case of polymerase chain reaction (PCR) samples, it is important to be able to separate smaller dimer and primer molecules from the main nucleic acid fragments in the sample and then isolate and collect the main nucleic acid fragments for further analysis or processing, while directing the smaller primer and dimer components to a waste reservoir/cell for removal and subsequent disposal.

Thus, it would be advantageous to provide improved microfluidic devices, systems and methods for use in separating sample materials into different sample components or fragments and then isolating one or more of the sample components for further processing or analysis in the device. Such devices preferably should employ configurations that optionally allow a sample material to be electrophoretically separated into sample components in a separation matrix within a separation conduit in the device. The sample components may then be detected in a detection zone in the separation conduit, and then selected fragments or components of interest shunted to a component collection conduit within the device downstream of the detection zone for further processing or analysis based on information (such as size-based information) received at the detection zone.

BRIEF SUMMARY OF THE INVENTION

Methods, devices, and integrated systems for use in separating sample materials into different sample components (based on the relative size of the sample components, for example) and then isolating one or more of the sample components for further processing or analysis are disclosed. In a first aspect of the present invention, the invention provides methods of isolating one or more sample components within a sample material source in a microfluidic device which comprises separating the sample components in a separation conduit located within the device, detecting the sample components at a detection zone in the separation conduit, and transporting selected one or more of the sample components to a sample component collection conduit in the device based on information received at the detection zone.

The method preferably employs a system that includes a substrate having a separation conduit having a separation matrix disposed therein. A detector is positioned in sensory communication with a detection zone in the separation conduit at a first location along a length of the separation conduit for detecting the one or more sample components in the separation conduit following separation in the presence of the separation matrix. A sample component collection conduit in the substrate is fabricated into the substrate in fluid communication with the separation conduit at a second location downstream from the first location. A processor which is operably coupled to the detector and to a fluid direction system is configured to control movement of sample components from the separation conduit into the sample component collection conduit based on information received from the detector. Specifically, the method comprises transporting a first sample material through the separation conduit to separate the first sample material into a plurality of sample components, detecting the plurality of sample components at the first location with the detector, and then moving a selected one or more of the plurality of sample components from the separation conduit into the sample component collection conduit in response to instructions from the processor to the fluid direction system. The processor, e.g., a computer, is programmed to record the data received from the detector, and to monitor and instruct the operation of the fluid direction system in accordance with a set of preprogrammed and/or user input instructions, e.g., which sample components of a particular size range should be diverted to the component collection conduit for further processing and analysis.

In a preferred aspect of the invention, the processor includes a computer which includes appropriate programming for receiving a signal from the detector that is indicative of a separated component passing the detector, determining a retention time of the separated components in the separation conduit, and determining a size of the separated components by comparing the retention time of the separated components to a retention time of components of a standard reference of known size for the sample material. A user can input instructions to the computer to direct the fluid direction system to move a selected one or more of the separated components of interest from the separation conduit into the sample component collection conduit based on the determined size of the selected one or more sample components. The standard reference of known size is obtained by separating a standard DNA sizing ladder, e.g., for DNA separations, or a standard polypeptide of known molecular weight, e.g., for protein separations. Typically, the step of separating a standard sizing ladder is performed prior to transporting the first sample material through the separation conduit to separate the first sample material into a plurality of first sample components. The reference standard sizing ladder can also be mixed with the sample material prior to the transporting step. Isolation of selected fragments of interest in the sample collection conduit can be done "on the fly" by programming the computer to direct the fluid direction system to move a selected one or more of the separated components of interest from the separation conduit into the sample component collection conduit in the same separation cycle. Alternatively, to minimize the potential impact of individual migration drift problems in the separation matrix when multiple samples are run through the device (which can render inaccurate proper selection and isolation of fragments of a particular size), the samples are typically co-run with flanking size markers of a known size (corresponding to the uppermost and lowermost bands of the sizing ladder) which allow accurate size calibration of every run. The computer is programmed to re-size the sample run data by calibrating the size of the known flanking markers to the sizing ladder as is well known to one of ordinary skill in the art. However, because the computer-controlled size calibration cannot be performed until after the sample has been completely fractionated into its individual bands and the upper and lower flanking markers have flowed past the detector, in some instances (particularly where multiple samples are run through the device), it may be necessary to run two or more sample materials through the separation conduit (from the same sample reservoir in the device, for example, or from a sample well in a multiwell plate accessed by an external pipettor or capillary element). The computer can be programmed to identify a selected component of interest (based on a comparison to the sizing curve) as corresponding to a particular peak in the fluorescence versus time curve (e.g., for fluorescence based detection schemes) for each of one or more additional samples run through the device based on the recalibrated sizing data. When a sample is run a second (or third or more) time through the device, the computer can be programmed, for that particular sample, to instruct the operation of the fluid direction controller to direct fluid movement into the collection conduit when a signal corresponding to that particular peak is registered by the detector. Thus, one can ensure that a fragment of a given size and amount is accurately shunted to the collection conduit.

The substrate preferably includes at least one sample loading conduit, for example two or more, for example five (or more), sample loading conduits, each having a loading end and a shared waste end, the loading end being contacted with the source of the sample material, the method further comprising electrokinetically moving the sample material into the loading end of the sample loading conduit and toward the waste end of the sample loading conduit by applying a voltage gradient along the length of the loading conduit, and/or by applying a first pressure difference across the sample loading conduit to move the sample material into the loading end of the sample loading conduit and toward the waste end of the sample loading conduit. The sample loading conduit and separation conduit are in fluid communication at a first fluid junction, and a portion of the sample material in the sample loading conduit is moved through the first fluid junction and into the separation conduit by applying a voltage difference through the fluid junction to electrokinetically move the sample material from the sample loading conduit into the separation conduit. The step of separating the sample material optionally comprises applying a voltage difference across the separation conduit in the presence of an appropriate separation matrix, to electrophoretically separate the sample material into one or more sample components.

The sample component collection conduit, in one aspect of the invention, is in fluid communication with at least one or more additional channels in the device which is/are fluidly coupled to one or more reagent reservoirs (or to an external pipettor, for example) which contains at least a first agent, and the method further comprises transporting an amount of the first agent into the sample component collection conduit to mix with the one or more sample components therein. The first agent may be selected from a variety of different materials, such as a plasmid, a diluent, a detergent, a mass spectrometer MALDI matrix, a buffer solution (e.g., containing ATP for a ligation reaction), a protein affinity label, a ligation agent, or a combination of one or more of the above agents (for example to initiate a ligation reaction between a sample nucleic acid fragment of a particular size and a plasmid in preparation for a cloning operation). The sample component collection conduit preferably is in fluid communication with at least one sample component reservoir or well in the device, for example two or more collection wells, for example five collection wells, the method further comprising transporting the one or more sample components to the at least one sample component well for collection and subsequent removal. The sample components or reaction mixture (in the case of a ligation reaction in the collection conduit, for example) can then be removed by the user for subsequent analysis (e.g., mass spectroscopy) or experimentation by optionally vortexing the device to homogenize the components therein to facilitate their removal from the sample well. The one or more sample component wells can be provided with a buffer solution, such as a low conductivity wash buffer, for example, so that the component samples can be washed and purified in the well(s) prior to removal therefrom.

In a related aspect of the invention, a microfluidic device for separating sample components from a sample material source and isolating one or more of the sample components is provided which generally comprises a substrate having at least one surface, and at least first and second channels fabricated into the surface of the substrate which intersect with each other at a first location along a length of the first channel, at least one of the first and second intersecting channels having at least one cross-sectional dimension in the range of from about 0.1 to about 500 μm. A sample material separation system is operably coupled to at least the first channel for controlling separation of the sample material into one or more sample components in the first channel in the presence of a separation matrix. A detection zone is located at a second location along the length of the first channel upstream from the first location wherein detection of the one or more sample components can occur. The device includes a fluid direction system operably coupled to at least the second channel for controlling movement of selected one or more sample components from the first channel into the second channel based on information received at the detection zone, such as sizing information. Although microfabricated fluid pumping and valving systems are readily employed in the devices of the invention, the cost and complexity associated with their manufacture and operation can generally prohibit their use in mass-produced and potentially disposable devices as are envisioned by the present invention. Thus, the devices of the present invention will typically include an electrokinetic fluid direction system. Such fluid direction systems combine the elegance of a fluid direction system devoid of moving parts, with an ease of manufacturing, fluid control and disposability. Examples of particularly preferred electrokinetic fluid direction systems include, e.g., those described in U.S. Pat. Nos. 6,046,056 and 5,976,336, the entire contents of which are incorporated by reference herein.

The present invention also provides an integrated system for isolating one or more sample components of a sample material following separation of the sample material into a plurality of sample components, which system generally comprises a substrate having at least one surface, and a separation conduit fabricated into the surface and having a separation matrix disposed therein.

A detector (such as an optical detector) is positioned in sensory communication with the separation conduit at a first location along a length of the separation conduit for detecting the one or more sample components in the separation conduit. A sample component collection conduit is fabricated into the surface and is in fluid communication with the separation conduit at a second location downstream from the first location. The substrate includes at least a fluid direction system for controlling movement of at least the sample components within at least the sample component collection conduit. A processor is operably coupled to the detector and the fluid direction system for instructing the fluid direction system to direct movement of one or more sample components from the separation conduit into the sample component collection conduit based on information received from the detector. The processor, e.g., a computer, is programmed to record the data received from the detector, and to monitor and instruct the operation of the fluid direction system in accordance with a set of preprogrammed and/or user input instructions, e.g., which sample components of a particular size range should be diverted to the component collection conduit for further processing and analysis. For example, the computer includes appropriate programming for receiving a signal from the detector that is indicative of a separated component passing the detector, determining a retention time of the separated components in the separation conduit, and determining a size of the separated components by comparing the retention time of the separated components to a retention time of components of a standard reference of known size for the sample material (such as a DNA sizing ladder for DNA separations). The computer is programmable by a user to control the fluid direction system to move a selected one or more of the separated components of interest from the separation conduit into the sample component collection conduit based on the determined size of the selected one or more sample components.

DETAILED DESCRIPTION OF THE INVENTION

I. General Aspects of the Invention

Figure 1A:
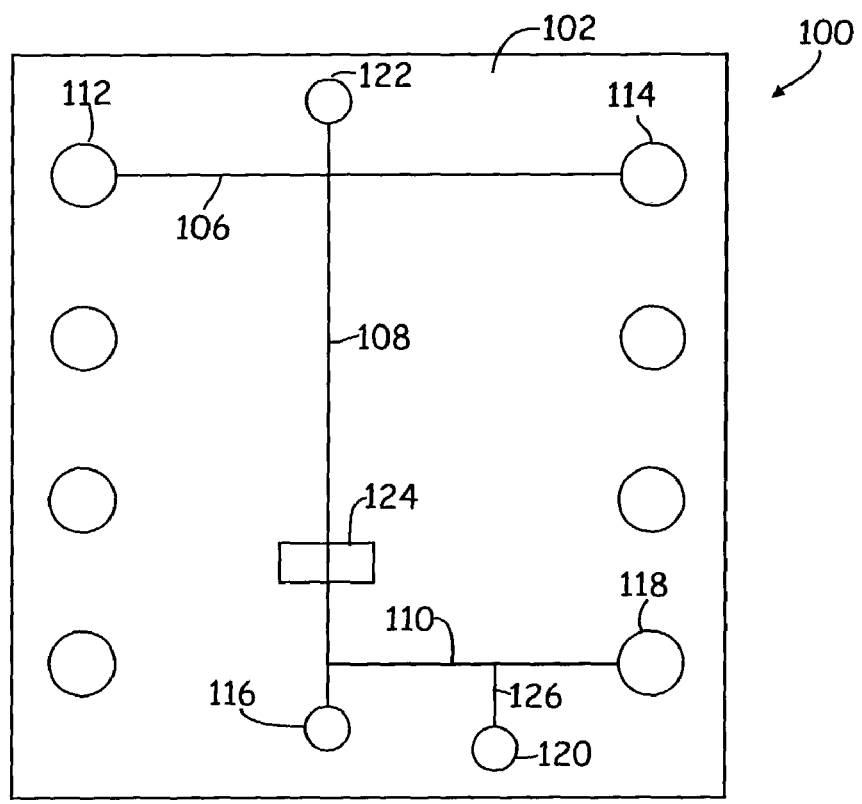
FIG. 1 is a schematic illustration of the layered construction of a portion of a simplified microfluidic device from the top (panel A), side (Panel B), and perspective views (panel C).

The present invention is generally directed to improved methods, devices and systems for performing in the same device analytical operations that include a separation function, e.g., employing a separation matrix, followed by an isolation function, e.g., shunting off or extracting selected components or fractions of a sample material of interest for further processing or analysis. In particular, these methods and systems are particularly suited for separation and isolation of nucleic acid fragments, protein fragments, or the like.

The present invention also provides methods for performing additional ligation or reaction steps on isolated fractions of a sample material following extraction from the separation conduit by, for example, intermixing such components with additional reagents, such as marker compounds, e.g., molecular weight standards, labeling compounds, MALDI matrixes, and the like, for mass spectroscopy, or ligation agents, such as ligase enzymes (e.g., Topo-isomerase), plasmids, and the like, for performing cloning operations. By combining the separation step with an isolation function, one eliminates additional sample fragment processing steps such as manual fragment extraction, staining, UV illumination, physical cutting, plasmid incorporation, and the like, that are typically carried out separately from the separation system, e.g., in multiwell plates or in individual test tubes.

A number of additional features are optionally included with the systems described herein for particular operations and manipulations, and these are generally described in greater detail below.

II. Definitions

Unless specifically indicated to the contrary, the following definitions supplement those in the art for the terms below.

"Microfluidic," as used herein, refers to a system or device having fluidic conduits or chambers that are generally fabricated at the micron to submicron scale, e.g., typically having at least one cross-sectional dimension in the range of from about 0.1 µm to about 500 µm. The microfluidic systems of the invention are fabricated from materials that are compatible with components of the fluids present in the particular experiment of interest. Customarily, such fluids are substantially aqueous in composition, but may comprise other agents or solvents such as alcohols, acetones, ethers, acids, alkanes, or esters. Frequently solvents such as dimethlysulfoxide (DMSO) or dimethylformamide (DSF) are used, either pure, or in aqueous mixture, to enhance the solubility of materials in the fluids. In addition, the conditions of the fluids are customarily controlled in each experiment. Such conditions include, but are not limited to, pH, temperature, ionic compositions and concentration, pressure, and application of electrical fields. The materials of the device are also chosen for their inertness to components of the experiment to be carried out in the device. Such materials include, but are not limited to, glass and other ceramics, quartz, silicon, and polymeric substrates, e.g., plastics, depending on the intended application.

A "microchannel" is a channel having at least one microscale dimension, as noted above. A microchannel optionally connects one or more additional structures for moving or containing fluidic or semi-fluidic (e.g., gel- or polymer solution-entrapped) components.

A "microwell plate" is a substrate comprising a plurality of regions which retain one or more fluidic components.

A "pipettor channel" is a channel in which components can be moved from a source to a microscale element such as a second channel or reservoir. The source can be internal or external (or both) to the main body of a microfluidic device comprising the pipettor channel.

III. Systems

In accordance with the present invention, systems are provided for use in performing separations and isolation of selected components or fragments of interest. As such, these systems typically employ a separation conduit that has disposed therein a separation matrix. At least one sample loading conduit is provided that is fluidly connected to the separation conduit and to one or more sample reservoirs/wells to permit delivery of one or more sample materials to the separation conduit wherein the separation operation, and typically detection, portion of the analysis takes place. At least one sample component collection conduit is fluidly connected to the separation conduit, typically downstream from the detection portion of the separation conduit, to permit separated components to be extracted from the separation conduit for further analysis or processing. The sample, separation, and collection conduits may take a variety of different forms, including simple tubing or capillaries joined together to form the interconnected conduits described herein. However, in preferred aspects, such systems are embodied within an integrated body structure or microfluidic device, wherein the conduits are fabricated in a monolithic substrate.

Typically, such body structures are fabricated in a layered structure where a first planar substrate is manufactured to include one or more grooves etched, carved, embossed, molded, or otherwise manufactured into a planar surface of the substrate. These grooves typically define the layout of at least a portion of the interconnected channel network of a microfluidic device's body structure. A second substrate layer is then overlaid and bonded to the planar surface of the first substrate to sealably enclose the grooves, and thereby define the enclosed conduits or channels of the device.

Figure 1B:
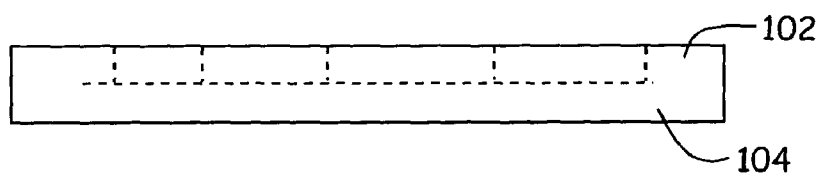
Figure 1C:
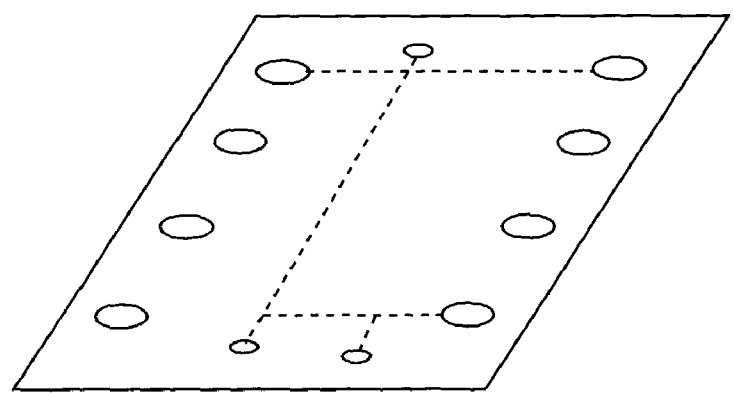

A schematic illustration of the layered construction of a portion of a simplified microfluidic device to illustrate the teachings of the present invention is shown in FIG. 1. The illustrated device is shown inverted as compared to normal operation for ease of illustration. As shown, the overall device 100 is fabricated from two planar substrate layers 102 and 104. Optionally, the device may also include a sampling element or capillary (not shown) that is attached to the finished structure. In fabricating the device shown, a network of grooves 106, 108, 110 is fabricated into the surface of substrate 102. The grooves can be fabricated into a variety of different configurations or network geometries depending upon the type of operation to which the device is to be put. As shown, each groove terminates in an aperture or port disposed through substrate 102, e.g., ports 112-122. When substrates 102 and 104 are mated together and bonded, the groove network is sealed to define an enclosed channel network. The ports 112-122 are sealed on one side to define fluid reservoirs and access points to the channel network. An assembled, properly oriented device is illustrated in FIG. 1B. In the simplified microfluidic device shown in FIG. 1, sealed groove 106 defines a sample loading conduit, groove 108 defines a separation conduit, and groove 110 defines a collection conduit for collecting extracted fragments of interest.

In accordance with the present invention, the sample loading conduit(s) 106, separation conduit 108, and collection conduit 110 are provided substantially within the integrated body structure. In particularly preferred aspects, these conduits are of microscale dimensions, meaning that they have at least one cross-sectional dimension that is less than 500 µm, e.g., between about 0.1 and about 500 µm, and preferably between about 1 µm and about 200 µm, and more preferably between about 1 µm and about 100 µm. Such integrated devices typically provide numerous advantages over larger-scale systems as a result of their precise tolerances and the accuracy with which their operations can be controlled.

The sample-loading conduit(s) 106, in addition to being in fluid communication with the separation conduit 108, is also in fluid communication with at least a first source of sample material. In the case of an integrated body structure, the source of sample material may be integrated with the body structure, e.g., as one or more reservoirs or wells 112 disposed in the body structure and in fluid communication with the loading channel. Alternatively, the source of sample material may be external to the body structure, e.g., a test tube, or well in a multiwell plate, which is placed into fluid communication with the sample loading conduit via a sampling pipettor or capillary element which is itself connected to or a part of the sample loading channel. The sample loading conduit 106 may be individually fluidly connected to a plurality of separate reservoirs via separate channels, as shown, for example, in FIG. 2 described below. The separate reservoirs may each contain a separate sample to be analyzed, such as various nucleic acid fragments or proteins, for example. The various sample materials are then transported from the various reservoirs into the sample channels using appropriate fluid direction schemes.

Figure 2:
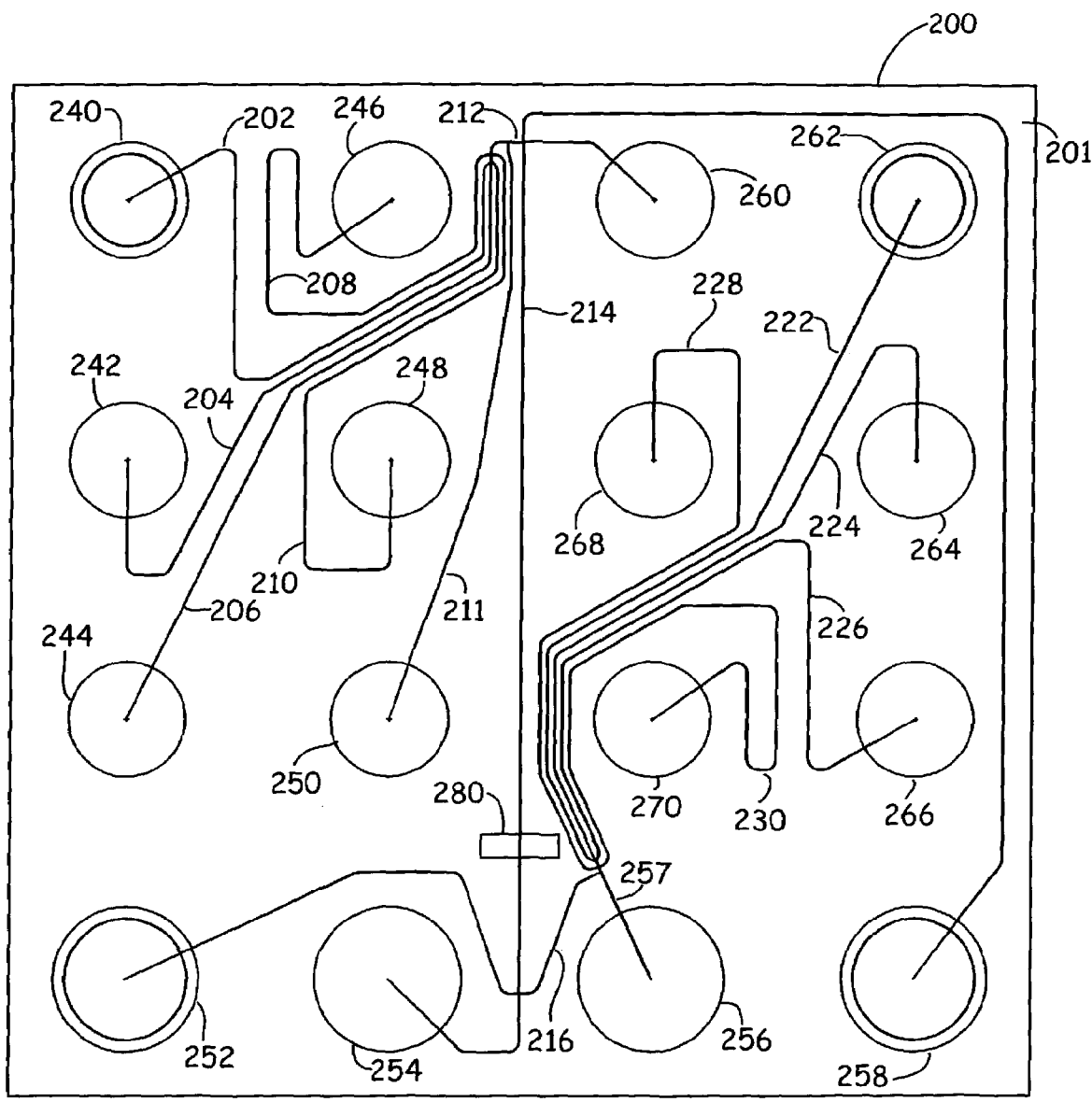
FIG. 2 is a channel layout for a microfluidic device that is particularly suited for performing the separations based analyses and isolation of separated components of the present invention.

An example of a microfluidic device that is particularly suited for practicing the present invention is illustrated in FIG. 2. As shown, the device 200 includes a main body structure 201. The body structure 201 houses a separation channel 214, a sample loading channel 212, and a collection conduit 216. As shown, the overall sample loading channel 212 is fluidly connected to five separate sample material reservoirs/wells 240, 242, 244, 246, and 248 via a channel network of separate channels 202, 204, 206, 208 and 210 respectively fluidly coupled to the wells. Although five sample reservoirs 240-248 are shown, the device may include more or less sample material wells depending on the particular design requirements of the system. Typically, the device will include at least four separate sample reservoirs, but can include five, six, seven or eight or more sample reservoirs. Additionally, although sample reservoirs 240-248 are shown all disposed on the same side of the separation conduit 214, it is to be understood that the multiple sample reservoirs can be disposed at locations on the substrate on both sides of the separation conduit (e.g., to minimize the distance, and thus the channel length and transit time, between any given reservoir and the point on the separation conduit 214 at which the sample is to be injected into that channel by, for example, clustering the sample reservoirs around the point at which the samples will be injected into the separation conduit 214).

Alternatively, the sample loading channel 212 may be fluidly coupled to one or more external sampling pipettors (not shown) or capillaries, having a capillary channel or conduit disposed therethrough, via a port (not shown). The pipettor is open at one end so as to be able to access sample materials from external storage vessels, e.g., test tubes, multiwell plates, etc. Sampling pipettors for microfluidic devices are described in detail in U.S. Pat. No. 5,779,868, which is incorporated herein by reference in its entirety for all purposes. Samples may be accessed via the pipettor or capillary element and moved into sample loading channel 212 and moved towards reservoir 260, e.g., by applying a vacuum at reservoir or pre-load well 250 (or another point in the system, e.g., reservoir 260) and/or by applying appropriate voltage gradients to an electrode placed in reservoir 250 (and/or 260) and an electrode operably coupled to the pipettor (as is the case for electropipettors as described in U.S. Pat. No. 5,779,868, for example). Alternatively, a vacuum can be applied through the capillary channel in the pipettor. The pipettor can be used, for example, to sip (by vacuum applied to reservoir 250, for example) various materials into the sample loading channel 212 to be used for performing subcloning steps in the device itself (e.g., in channel 212) prior to injecting the sample material into the separation conduit. For example, a vacuum can be applied to the capillary channel of the pipettor to draw various DNA PCR product samples into channel 212 from the sample wells of one or more multiwell plates (e.g., 96 or 384 well plates), where the DNA samples can then be combined with all the necessary enzymes and accessory reagents (supplied via one or more of wells 240-248 in the device) which are required for various pre-cloning DNA modifications (e.g., DNA blunting by conversion of 3' and 5' overhangs to blunt or flush ends, dephosphorylations, phosphorylations, etc.). Thus, for example, the DNA or vector termini can be blunted with Klenow fragments in the sample loading channel 212. The resulting blunt-ended DNA can then be separated in the separation conduit 214, and then components of it isolated and ligated efficiently into a vector in the sample component collection conduit 216 using the methods described in more detail below. Alternatively, both the DNA samples and any of the enzymes and reagents required for precloning steps can be loaded into one or more of the sample collection wells 240-248, and combined in the sample loading channel 212 to perform DNA blunting and other possible subcloning steps without the use of an external pipettor. The ligation of adaptors or linkers, when necessary during the cloning procedure, can also be performed in the sample loading channel. Materials brought into the sample loading channel 212 can then be moved towards the intersection of the sample loading channel with the separation conduit 214 by applying an appropriate voltage gradient to electrodes placed in reservoir 260 and one or more of wells 240-250 as is described further below.

Figure 3:
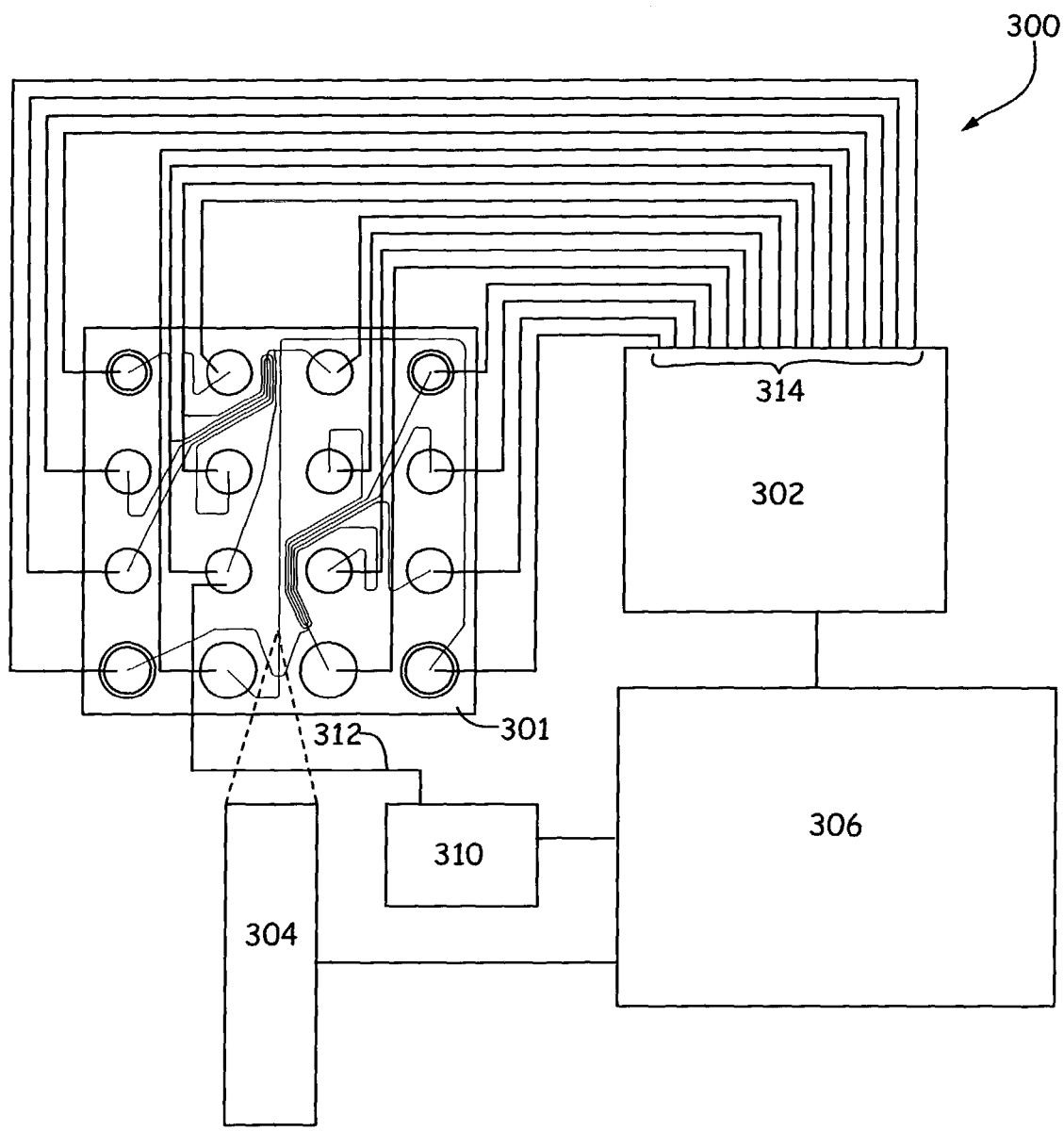
FIG. 3 is a schematic representation of an overall system including a microfluidic device, a controller, a detector, an optional vacuum source, and a processor.
Figure 4A:
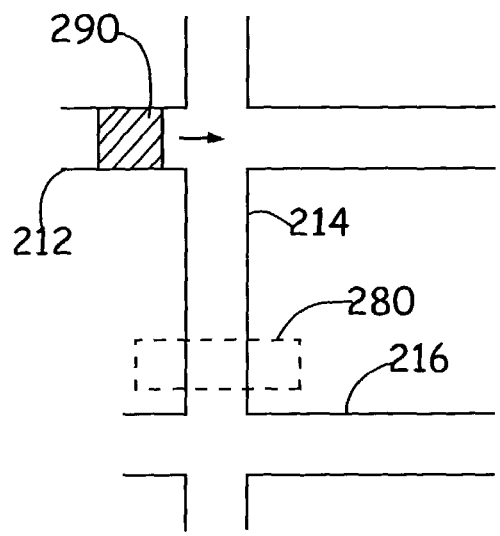
FIGS. 4A-D are schematic illustrations of an exploded view of a portion of the device shown in FIG. 2 performing separation of a sample into component fragments followed by a component isolation step.
Figure 4B:
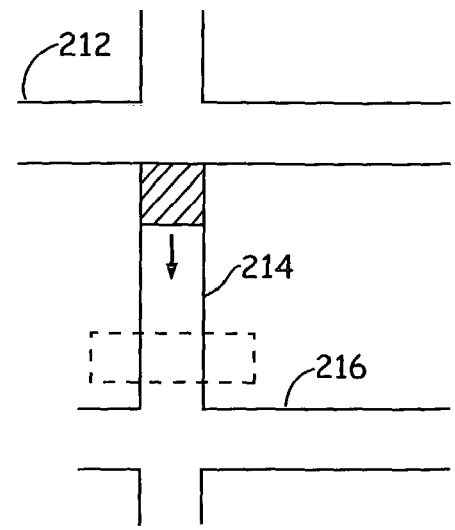
Figure 4C:
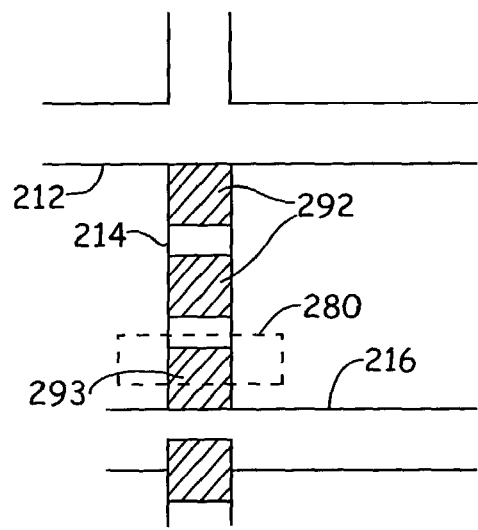
Figure 4D:
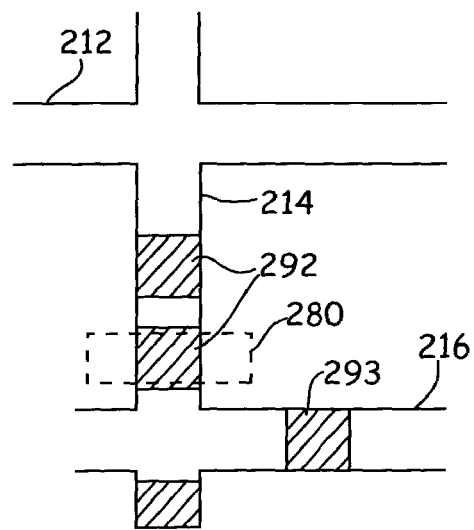

As shown, separation channel 214 is in communication with a buffer/gel reservoir 258 at one end and at a waste reservoir 254 at the other end. In addition to providing reservoirs for buffer, separation matrix, dye materials, and waste materials following analysis, these reservoirs also provide electrical access for electrophoretic separations. Specifically, electrodes are placed into contact with fluids in, e.g., reservoirs 254 and 258, in order to apply the requisite current through the separation channel 214 to electrophoretically separate the sample material into various fractions, or constituent elements. Separation channel 214 may also be fluidly connected to one or more additional buffer/matrix reservoirs, e.g., reservoirs 252 and 260, for supplying additional separation matrix, buffer materials, and the like to the separation channel 214. Similarly, as shown, sample loading channel 212 is fluidly connected at one end to the five sample material reservoirs 240, 242, 244, 246, and 248 (or to one or a plurality of external pipettors (not shown)), and at the other end to a buffer/waste reservoir 260. Employment of multiple sample reservoirs 240-248 provides the advantage of being able to serially separate and isolate fragments from multiple samples without having to manually load each sample after the analysis of a previous sample has concluded. The buffer/waste reservoir 260 preferably includes an electrode (shown in FIG. 3) disposed therein to allow sample materials to be transported from the sample wells 240-248 towards the reservoir 260 (and across the intersection of loading conduit 212 with separation conduit 214) by application of a voltage gradient to the electrode in reservoir 260 and a corresponding electrode in the sample wells 240-248. Optionally, reservoir 260 (and/or reservoir 250) provides an access port for a vacuum source to draw sample materials into the sample loading channel 212 from one of the sample wells 240-248 (via the channel network 202-210) via pressure-based fluid flow. In certain cases, sample materials and/or other materials such as separation matrix, buffers, and the like may be driven either by application of a vacuum to one of reservoirs 250 or 260, or by application of positive pressure to the sample material or reagent reservoirs 240-248, or a combination of the two. As in the case of the separation and sample loading channels, the illustrated reservoir 260 optionally provides storage for buffers and/or waste materials, and also provides access to the channels of the device to control movement of material from the sample loading channel 212 into the separation channel 214 (also termed "injection" of the sample material). Separation channel 214 comprises a detection window 280 for detecting a signal generated by materials flowing within the system. An additional preload channel 211 and reservoir 250 is provided in fluid communication with the sample loading channel 212 on the same side as the samples to be loaded, to permit preloading of one sample while a previous sample is being transported along the separation channel 214, e.g., by electrokinetically flowing a sample from one of wells 240-248 to the load/waste well 250 on the same side of the intersection of channel 212 with separation conduit 214, and thus not crossing the intersection. A sample component collection conduit 216 is also provided to collect isolated fragments of materials of interest, which is fluidly connected to separation channel 214 downstream from detection window 280. The collection conduit 216 is optionally coupled to one or more collection reservoirs 262, 264, 266, 268, and 270 via channel network 222, 224, 226, 228, and 230 for collection of separated fragments or fragment products, such as plasmid inserts.

Preferably, one or more additional reagent reservoirs, e.g., reservoir 256, may be provided within the integrated body structure 201 of the device 200 and fluidly coupled to collection conduit 216. These one or more additional reservoirs 256 provide additional reagents that may be used in further processing or analysis preparation of the fragments of interest in collection conduit 216 (or in any one of collection wells 262-270). Examples of such reagents include, e.g., internal standards, e.g., molecular weight markers for size based separations, labeling compounds, e.g., intercalating dyes, affinity labels, or the like, diluents, buffers (e.g., buffer with ATP for DNA ligase reactions), ligase enzymes for plasmid reactions (e.g., T4 DNA ligase or Topo-isomerase), MALDI matrix materials for mass spectroscopy analysis, isotonic salt solutions for compatibility with cells, etc. The reagent reservoir 256 is fluidly connected to the sample component collection channel 216 via a reagent introduction channel 257. Although not specifically shown in FIG. 2 or 4, additional post separation reactions are also preferably performed in accordance with the methods and systems described herein, including post separation labeling, ligation, heating, or the like. These post-separation reactions can optionally be performed in collection conduit 216 or in any one of the collection reservoirs 262-270.

In one aspect of the present invention, for example, selected fragments of DNA can be incorporated into plasmids in the collection conduit 216 (or collection wells 262-270 or their corresponding microchannels 222-230) by administering a plasmid into the collection conduit from reservoir 256. Thus, fragments of foreign DNA can be cloned in a linearized plasmid vector bearing compatible ends by the activity of Bacteriophage T4 DNA Ligase, which can also be provided via reagent reservoir 256. The enzyme will catalyze the formation of a phosphodiester bond between adjacent nucleotides if one nucleotide contains a 5'-phophate group and the other nucleotide contains a 3'-hydroxyl group. The plasmid DNA can be then be collected in one of the collection reservoirs 262-270, extracted, and introduced into modified bacteria (called competent cells) by the process of transformation.

In certain preferred aspects, e.g., in protein separations, a post separation dilution step is employed to dilute out the amount of detergent, i.e., SDS, to below a critical micellar concentration, in order to optimize the detection of labeled proteins versus-the free detergent micelles. Such post column treatments are described in detail in U.S. patent application Ser. No. 09/243,149, filed Feb. 2, 2000, and incorporated herein by reference in its entirety for all purposes. In such protein separation methods, the separation matrix includes a separation buffer, where the separation buffer typically includes a non-crosslinked polymer solution, a buffering agent, a detergent and a lipophilic dye. Non-crosslinked polymer solutions that are suitable for use in protein separations according to the present invention are described, for example, in commonly owned U.S. application Ser. No. 08/992,239, filed Dec. 11, 1997, which is incorporated by reference herein in its entirety. Preferably, the detergent and buffering agent are present within the separation buffer at concentrations that are at or below the critical micelle concentration ("CMC"). In this way, adverse effects such as dye binding to detergent micelles can be minimized.

In addition to the microfluidic device, the systems of the invention optionally include additional components, such as flow controllers for flowing sample materials into the sample loading channel, electrical controllers for applying currents through the separation channels (and optionally the injection channels), and detection systems for detecting separated sample material fractions.

Flow controllers typically include one or more variable or constant pressure or vacuum sources along with an interface for operably coupling the sources to the reservoirs. Such interfaces typically include ports with sealing gaskets, O-rings, insertion couplers, or the like, for providing a sealed connection between the pressure or vacuum source and the reservoir or port. The pressure or vacuum sources may apply a fixed or variable pressure, depending upon the particular operation that is to be performed. Fixed and variable pressure and vacuum sources are well known and include, e.g., peristaltic pumps, syringe pumps, diaphragm pumps, and the like. The pressure and/or vacuum sources are typically coupled to one or more different reservoirs on a device to control pressures at one or more reservoirs. Examples of multi-reservoir independent pressure controllers are described in, e.g., U.S. patent application No. 60/184,390, filed Feb. 23, 2000, and incorporated herein by reference in its entirety for all purposes. Fluid control is preferably controlled using electrokinetic forces, e.g., electroosmosis, through the inclusion of integrated or external electroosmotic pumping systems. Examples of electroosmotic pumps are described in U.S. Pat. No. 6,012,902, which is incorporated herein by reference in its entirety for all purposes. A variety of other fluid flow methods are also optionally used in practicing the present invention. For example, centrifugal forces may be employed to direct fluid movement where channel networks are fabricated into a rotor shaped body, where the direction of flow extends radially outward from the center of the rotor. Similarly, wall shear methods can be used to flow fluids, e.g., by moving two opposing surfaces relative to each other. Capillary forces are also optionally employed to cause fluid movement in channel networks (see, e.g., U.S. patent application Ser. No. 09/245,627, filed Feb. 5, 1999, which is incorporated herein by reference in its entirety). Other fluid flow methods include gas generation techniques or fluid/gas expansion/contraction methods based upon temperature changes, see, e.g., U.S. Pat. No. 6,043,080 to Lipshutz et al., which is also incorporated herein by reference in its entirety for all purposes.

In addition to controlling fluid flow during the sample loading process, the systems of the present invention also include controller aspects for controlling the injection of sample material into the separation conduit as well as moving sample materials through the separation conduit to accomplish the desired separation/fractionation. As noted above, the injection and separation operations are optionally carried out using pressure based or bulk fluid movement methods, e.g., sample is injected using pressure and separated through an appropriate separation matrix using pressure-based or bulk flow of the fluid containing the sample materials. In such cases, the flow controllers described above are simply expanded to control flow within these additional portions of the microfluidic device. In preferred aspects, however, at least one of the injection and separation operations are carried out by the electrophoretic movement of sample materials, e.g., in the absence of substantial bulk flow.

In such cases, the controllers for these operations typically include electrical power supplies coupled via appropriate circuitry to an electrical interface that delivers electrical current through the appropriate conduits of the system, e.g., the sample loading, separation and/or collection conduits. Typically, these interfaces comprise electrode pins that are positioned on the interface component of the controller to be inserted into the reservoirs of the device. However, optionally, the interfaces comprise electrical contacts, e.g., contact pads, insertion couplers, or the like, that interface with electrical contacts on the body structure of the device that includes the separation conduit. These contacts then deliver current through the appropriate conduits via electrical circuitry disposed on or within the body structure, which circuitry delivers voltages to reservoirs or conduits. Examples of different interfacing scenarios are described in U.S. Pat. No. 5,955,028, which is incorporated herein by reference in its entirety for all purposes.

In addition to control components, the systems of the present invention also typically include detection systems for detecting the separated fractions of the sample material within the separation channel, i.e., following separation. Detection systems may be based upon a variety of well known detection methods, including fluorescence spectroscopy (laser induced and non-laser methods), UV spectroscopy, electrochemical detection, thermal detection, capacitance based detection (see Published PCT Application No. WO 99/39190), mass spectrometry based detection, e.g., MALDI-TOF and electrospray, which can be readily configured to receive materials directly from capillary or microfluidic device outlets, and the like. In preferred aspects, optical detection methods, and particularly fluorescence based detection methods are used. Such detection systems generally include an excitation light source that provides light at an appropriate wavelength to excite the particular fluorescent species that is to be detected. The excitation light is then transmitted through an appropriate optical train, including lenses, filters (e.g., wavelength and/or spatial filters), beamsplitters, etc., and directed through, e.g., an objective lens, at a translucent portion of the separation conduit. As fluorescent species, constituents or fractions of the sample material pass through the excitation light, they fluoresce. The fluorescent emissions are then collected and transmitted back through the objective lens and the same or an alternate optical train to a light sensor, e.g., a photodiode, photomultiplier tube, CCD or the like. The device may also include one or more light altering optical elements (such as a lens or optical filter) integrated into the body structure of the device as is more fully described in U.S. Pat. No. 6,100,531 assigned to the same assignee of the present invention, the entire contents of which are incorporated by reference herein. Such devices with integrated optical elements perform at least a portion of the optical manipulations used in the optical detection scheme employed.

The systems also include a processor, e.g., a computer, that is programmed to record the data received from the detector, and optionally analyze the data, e.g., integrate peaks, calculate retention times, calibrate separations with internal standards, etc. The processor is also preferably programmed to monitor and instruct the operation of the fluid flow controllers in accordance with a set of preprogrammed and/or user input instructions, e.g., which sample components of interest of a particular size range should be diverted to the component collection conduit for further processing and analysis.

A number of other components are also optionally added to the systems described herein depending upon the particular applications that are being performed, including, e.g., temperature control element, e.g., heating and cooling elements for heating and/or cooling portions of the devices described herein, robotic components for moving sample plates and/or devices around to access different materials and/or functionalities of the overall system. In general, all of these additional components are commercially available and are readily adapted to the systems described herein.

A schematic illustration of an overall system, as described above, is shown in FIG. 3. As shown, the system 300 includes a microfluidic device 301, e.g., as illustrated in FIG. 2. The microfluidic device 301 is typically operably coupled to an electroosmotic flow controller system 302. This flow controller 302 applies appropriate motive forces to the materials within the channels of the device 301 to carry out a desired operation. The controller 302 generally includes an electrical power supply (and/or a pressure and/or vacuum source). The electrical power supply is coupled to the channels of the device through which electrokinetic movement is desired, e.g., separation channel 214 and/or sample loading channel 212 and collection conduit 216, e.g., via reservoirs 254 and 258, or any one of reservoirs 240-248, 250, 252, 256, 260-270, respectively, e.g., using electrical connectors 314 which are connected to or are themselves, the electrodes that are disposed in the reservoirs to contact the fluid therein. If used (for example, in conjunction with an external pipettor coupled to sample loading conduit 212), a separate pressure/vacuum source 310 can be coupled to the channels through which pressure induced flow is desired, e.g., channels 211, 212 and/or 216. For example, a single vacuum source 310 can be connected to reservoir 250 (or 260) via vacuum line 312, to draw material into and through channel 212 from an external pipettor (not shown) fluidly coupled to channel 212 (and/or from any of the sample reservoirs 240-248 which contain up to a total five different sample sources). Alternatively, the vacuum source (if used) can be integrated into the flow controller system 302 as an integral unit thereof. As noted, electrical coupling is generally carried out via electrodes that are connected to the power supply and dipped into the reservoirs of the device. Pressure/vacuum connections typically involve the use of a sealing pressure connection, e.g., that employs a gasket or o-ring, to communicate pressure to a reservoir. In general, these types of instrument/device interfaces are described in U.S. Pat. Nos. 5,955,028, and 6,071,478, each of which is incorporated herein by reference in its entirety for all purposes. Pressure or vacuum sources are generally widely available and will vary depending upon the needs of a particular application. Typically, for microfluidic applications, positive displacement pumps, e.g., syringe pumps and the like, are employed as pressure or vacuum sources. A variety of other pumps including peristaltic, diaphragm and other pumps are as readily employed.

A detector 304 is also employed in the overall system. The detector is typically placed within sensory communication of one or more of the channels of the device. As used herein, the phrase "within sensory communication" refers to positioning of a detector such that it is capable of receiving a detectable signal from the contents of a channel. In the case of optical signals, this only requires that the detector be positioned to receive optical signals from the material within a channel. This is generally accomplished by positioning an optical detector adjacent to a transparent or translucent portion of a channel segment such that it can receive the optical signal. Optical detectors are generally well known in the art and include fluorescence based detectors (intensity and polarization), spectrophotometric detectors, optical scattering detectors, and the like. For other detection schemes, e.g., electrochemical detection, the detector, or a portion of the detector is often placed into physical contact with the fluids within the channel containing device, e.g., via electrodes, semiconductor based sensors or microelectromechanical sensors (MEMS). Alternate detectors are also optionally employed in the methods described herein, including 'out-of-channel' detection schemes, e.g., mass spectrometry based detection, through MALDI-TOF or electrospray mass spectrometry methods. These detection schemes also have been previously described.

In addition to detector 304, controller 302 and device 301, an overall system preferably includes a computer or processor 306, which is operably coupled to controller 302 and detector 304. The computer is typically connected both to the detector 304 and the controller 302 (an vacuum source 310 if provided). The computer includes programming to record the data received from the detector, and to monitor and instruct the operation of the fluid direction system 302 in accordance with a set of preprogrammed and/or user input instructions, e.g., which sample components of a particular size range should be diverted to the component collection conduit for further processing and analysis. Additionally, computer 306 also is programmed to receive and record data from detector 304 and optionally analyze the data and produce a user comprehensible output or report.

Systems optionally employ sample accessing systems, e.g., robotic x-y-z translation stages and other multiwell plate handling equipment for delivering a sample material well to the sampling element of a microfluidic device, e.g., so that a capillary (if part of the device) can be immersed in a sample material, and access multiple different wells on a single plate as well as multiple plates. Commercially available systems include, e.g., Carl Creative conveyor systems, as well as Twister systems available from Zymark Inc. and robotic x-y-z translation arms, e.g., as available from Parker Positioning Systems, Inc.

III. Electrophoretic Separations and Isolation of Desired Separated Components

As stated above, in preferred aspects, the systems and methods of the present invention isolate desired components of a sample material following separation of the sample material into its various components (by size or weight, for example). For example, in DNA separations, it is often desirable to separate and isolate DNA fragments of a particular length (e.g., number of base pairs) to incorporate such DNA fragment of interest in a plasmid for subsequent cloning experiments. The basic principle of isolation relies on a system being able to detect the component of a particular size (and/or molecular weight) and then synchronize the flow pattern such that the desired components are directed to the component collection conduit. Depending on the design of a given device and the specific application, the time delay between the detection of a signal and the onset of pressure pattern changes could vary. Generally speaking, one needs to allow some time for a desired component to flow down from the optical detection point to the intersection where the collection channel intersects with the main separation channel.

In operation, initially a separation matrix is introduced into or is already associated with the separation channel 214, e.g., coated during fabrication. Where a separation matrix is introduced into the separation channel, it is generally placed into one of reservoirs 252, 254, 258, or 260 (FIG. 2) and allowed to wick into the separation channel, with or without additional applied pressure. Typically, separation matrices are provided as liquid media or slurries of solid phase media, e.g., beads. Such separation matrices may include gels, such as polyacrylamide, agarose, or the like, or they may include liquid, dynamic separation matrices. Such dynamic matrices typically include polymer solutions, similar to those used in gel based media, but in a non-crosslinked format. Particularly useful dynamic matrices include cellulose polymers such as hydroxymethyl cellulose (HMC), hydroxypropylmethyl cellulose (HPMC), and preferably, acrylamide polymer solutions, such as linear polyacrylamide, polydimethylacrylamide, in both charged and uncharged conformations, and the like. These separation media are introduced into the separation column and provide a matrix through which the species within the sample material are separated, e.g., based upon their relative resistance to passing through the matrix. Examples of suitable separation matrixes to be used with the present invention include those disclosed in U.S. Pat. Nos. 5,958,694 and 6,032,710, which have been previously incorporated by reference herein. In protein separations, preferably a separation matrix comprising a separation buffer is used, which buffer comprises a non-crosslinked polymer solution such as described, for example, in commonly owned U.S. patent application Ser. No. 09/243,149, previously incorporated by reference herein. In preferred aspects, separation matrix is added to the separation channel of the device prior to adding any additional fluid components. Buffers and other fluids are then added to the appropriate channels of the device by pressure flow, which forces the matrix out of those channels. Alternatively, separation matrix may be added after the entire system is filled with a buffer, e.g., by bulk flowing the matrix primarily into the separation channel.

In order to accurately extract a separated component of a particular size, first, an appropriate standard sizing ladder is added to one of the sample wells 240-248 and run through the separation channel 214. The sizing ladder enables the size of unknown fragments to be determined. A commonly used standard is restricted wild type lambda DNA cut with HindIII which gives twelve fragments with a good size range. In addition, sizing ladders can be made by ligating DNA fragments together to form a series of bands, such sizing ladders being commercially available from Bioventures, Inc. (Murfreesboro, Tenn.), for example. An internal size standard provides accurate and reproducible size determination and quantification, and eliminates problems associated with run-to-run electrophoretic variability.

After the sizing ladder sample has been separated and all the bands have been detected at detection window 280 by detector 304, the electrode current can be switched to move a first sample into position from one of the sample wells 240-248. Sample material is then drawn into the sample loading channel 212, e.g., by drawing a sample material in fluid out of one of the sample reservoirs 240, 242, 244, 246, or 248 and into sample loading channel 212 electrokinetically by applying a voltage potential between well 260 and one or more of sample wells 240-248, as is described in U.S. Pat. No. 5,976,336, for example, which was previously incorporated herein by reference in its entirety for all purposes. Alternatively, in the case of a sipper chip, for example, materials can be moved into sample loading channel by applying a vacuum to reservoir 250 (and/or reservoir 260), whereby the flow of the materials is achieved by applying a pressure differential through the channels, e.g., by applying a vacuum to reservoir 250 and/or by applying a positive pressure to one of the sample wells 240-248. During the sample loading process, any separation matrix that has entered the sample loading channel 212 is washed away by the bulk flow of the sample material. Following injection of the sample material through the intersection of channel 212 and separation channel 214, an electrical current is applied through the length of the separation channel to electrokinetically move the sample material at the intersection into and through the separation channel. In preferred aspects, a slight current is supplied back through the portions of channel 212 that meet with separation channel 214, in order to push back sample material from the intersection. This improves separation efficiencies by eliminating substantial leakage that can contaminate the separation run. As the sample material (e.g., sample material 290 in FIG. 4A) is electrophoresed through the sample matrix in the separation channel, it is separated into fractions, e.g., fractions 292 in FIGS. 4C-D, that differ based upon their molecular weights.

Where one is separating nucleic acids, the highly uniformly charged nature results in all of the nucleic acid species in the sample material having the same electrophoretic mobility under an applied electric field, e.g., the charge to mass ratio of nucleic acids is constant. Inclusion of a viscous matrix in the separation column imparts differential mobility to the different species based upon their relative size, e.g., smaller molecules move more easily through the viscous matrix than do larger molecules, allowing their separation despite their shared charge to mass ratio. For protein or peptide based separations, electrophoretic size based separation is more complex due to the highly variable charge to mass ratios of different proteins and peptides. As such, such separation is typically accomplished by imparting a substantially uniform charge to the macromolecules by treating those macromolecules with a highly charged molecule, e.g., detergents like SDS, and the like. The association of the protein or peptide molecules with the detergent allows a relatively uniform movement, e.g., magnitude and direction, of all of the protein molecules in a mixture. As with nucleic acid separations, differential mobilities are imparted by virtue of incorporation of a viscous matrix through which different sized molecules will move at different rates.

The systems and methods of the present invention can also be used to separate and isolate plasmid topological isomers. Plasmids of identical sequences may exist in different topological isomers. Plasmid samples prepared from bacteria are commonly a mixture of the covalently closed circular (ccc) form, the open circular (oc) form and the linear form. The conventional method of plasmid sizing involves multiple steps including converting the plasmid to its linearized form. However, because the different plasmid forms differ in compactness of their 3D structure, they migrate differently in a separation gel matrix during electrophoresis. The migration order for all plasmids, because of their differing sizes, typically would be the supercoiled ccc molecules appearing first, followed by the linearized plasmid, and then the open circle form. The relative amount of the plasmid isoforms in different samples of the same plasmid can be compared. If the standard of a supercoiled plasmid is available, then the concentration of the supercoiled form in the plasmid preparation can be estimated in a broad range of sample concentrations of 1 to 100 ng/μl. With the use of an external supercoiled DNA ladder, the plasmid sample can be sized with high precision. The determination of the relative sizes of plasmids is enough for a large number of applications. One such application is the screening (and isolation) for clones that contain target insert (s) on a cloning vector by comparing the resulting clones size to that of the cloning vector.

The separated components of interest are then flowed past the detection window 280 in order to detect the components of a particular size as shown, for example, in FIGS. 4A-D. In the case of fluorescent detection, typically a laser activated fluorescent detection system monitors the flowing fragments at detection region 280. The macromolecules in the sample (e.g., nucleic acid fragments such as DNA) have a fluorescent or fluorogenic labeling group coupled to them. For instance, in the case of nucleic acids, a variety of fluorescent labeling techniques can be used. These are generally well known in the art, and include the use of covalently attached fluorescent labeling groups, e.g., as described in U.S. Pat. Nos. 4,711,955, 5,171,534, 5,187,085, 5,188,934, and 5,366,860, all of which are hereby incorporated by reference herein in their entirety for all purposes. Alternatively, associative labeling groups may be used, which preferentially associate with the macromolecular species of interest, or are only detectable, e.g., fluorescent or fluorogenic, when associated with the macromolecules of interest. Examples of such labeling groups include, e.g., intercalating dyes for double stranded nucleic acids, streptavidin/biotin labeling groups, and the like. As noted, preferred aspects of the present invention utilize fluorescent detection systems. Typically, such systems utilize a light source capable of directing light energy at the separation channel as the separated macromolecular species are transported past. The light source typically produces light of an appropriate wavelength to activate the labeling group. Fluoresced light from the labeling group is then collected by appropriate optics, e.g., an objective lens, located adjacent the detection window 280 in separation channel 214, and the collected light is directed at a photometric detector, such as a photodiode or photomultiplier tube. The computer 306 is coupled to the detector and receives the data from the detector and records that data for subsequent storage and analysis. The computer is programmed to use the size standard to create a sizing curve (based on size versus time through the separation conduit 214), and then determines the length of each dye-labeled fragment by comparing it with the sizing curve. A user can input instructions to the computer to select a fragment of a particular size/length (e.g., fragment 293 in FIGS. 4C-D) to be shunted to the collection conduit 216 for further analysis or processing in the device, by virtue of the relative amount of time it took the different bands to travel through the separation column, e.g., relative to standards of known characteristics such as size, molecular weight or charge.

Then, when such separated fragment of a particular size of interest is detected (based on comparisons to the sizing curve which is generated by the computer), the computer includes programming to instruct the operation of the flow controller 302 to direct fluid movement through the collection conduit 216 in accordance with the user specified instructions. In controlled electrokinetic transport, the separated component of interest (e.g., fragment 293 in FIGS. 4C-D) is moved into the collection conduit by applying a voltage gradient along the path of material flow, e.g., by applying a voltage potential between electrodes positioned in well 252 and one of wells 262-270. In order to ensure that only fragment 293 is shunted into the collection conduit 216 (and that there is no cross-contamination from one or more of the other fragments 292), the voltage gradient applied to separation conduit 214 generally must be tightly regulated, e.g., temporarily stopped and then reinitiated only after fragment 293 reaches one of collection wells 262-270, to avoid inadvertent shunting of other separated components 292 into the collection conduit during this injection period. Where the material path length to any of collection wells 262-270 is relatively long, as it is, for example, for well 262 (which is fluidly coupled to collection conduit 216 via relatively long channel segment 222), this delay in placing the separation conduit in an "off" mode can be appreciable, which can significantly decrease the throughout of the system (particularly where multiple samples are run through the device).

To offset this delay, reservoir 256 (or another similar reservoir which is not shown) can be fluidly coupled to collection conduit 216 near to the intersection of the collection conduit with the separation conduit. In this way, when the separated component reaches a point downstream of the intersection of reservoir 256 (or other similar reservoir) with collection conduit 216, a voltage gradient can then be switched from the electrode coupled to reservoir 252 and applied to an electrode placed in reservoir 256 (or other similar reservoir) and the electrode placed in one of the respective collection wells 262-270, to drive the separated component along the remainder of the material path length to one of those wells. At that point, an electrical current can then be rapidly reapplied through the length of the separation channel to electrokinetically move additional sample material through the separation channel. The amount of time that a separated component of interest travels through collection conduit 246 upstream from the intersection of reservoir 256 (or other similar reservoir) with conduit 216, and the voltage gradient applied to collection conduit 216, generally dictates the amount of time that no electrical current can be applied through the length of the separation channel, particularly where the separated components are spaced closely together from each other. Thus, by fluidly coupling reservoir 256 (or another similar reservoir) to conduit 216 as close as possible to the intersection of collection conduit 216 with separation conduit 214, the amount of time that separation conduit will be in an "off" mode can be minimized and the throughput of the system correspondingly increased. The width of the collection conduit generally will determine the discrimination/resolution of the shunted fragment in the collection conduit. For example, if voltage applied along the length of the separation conduit is turned off when the fragment of interest is in the separation/shunt intersection, and then voltage applied along only the length (or a portion thereof) of the collection conduit, a slug approximately the width of the collection channel would be driven into the collection channel. Thus, the wider the collection channel the less discriminating it would be. Thus, the width of the collection channel can be varied from one device to another to increase or decrease the discrimination of the system based on the discrimination required for a chosen sample material.

Once the desired separated component (e.g., fragment 293) reaches one of collection wells 262-270, it is then ready for further processing, analysis, or collection in one of those collection wells. As each of one or more samples is run, real-tine data may be displayed on the computer monitor in the form of an electrophemogram (trace of fluorescence vs. time), a simulated gel picture, and a data table that includes information about fragment size and concentration.

Figure 5A:
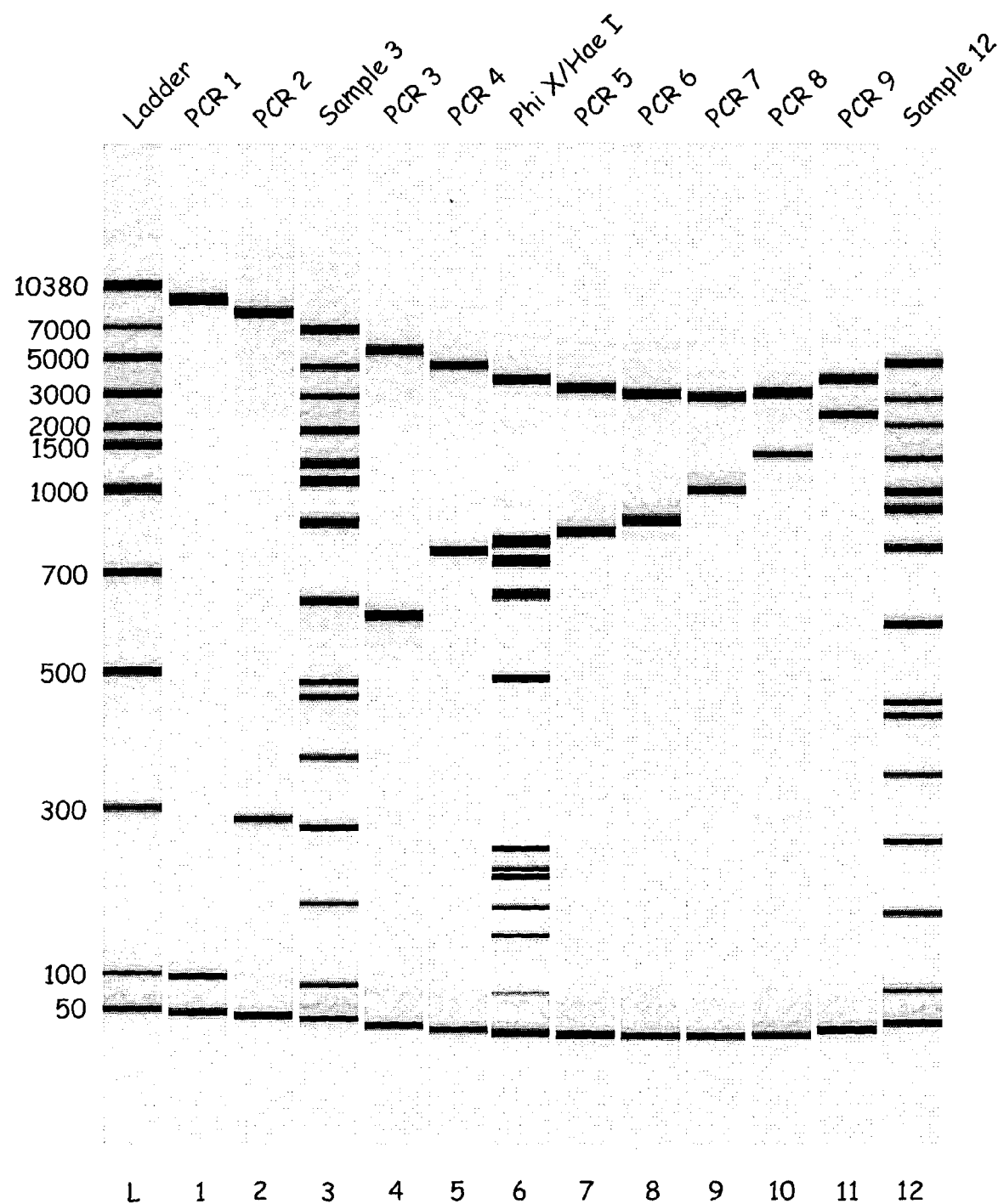
FIGS. 5A-B are representative computer-generated DNA band plots showing fluorescence versus time measurements in DNA band plot form, and illustrating the effect of band migration (FIG. 5A) and subsequent recalibration of the band data based on comparisons to a standard DNA sizing ladder (FIG. 5B).
Figure 5B:
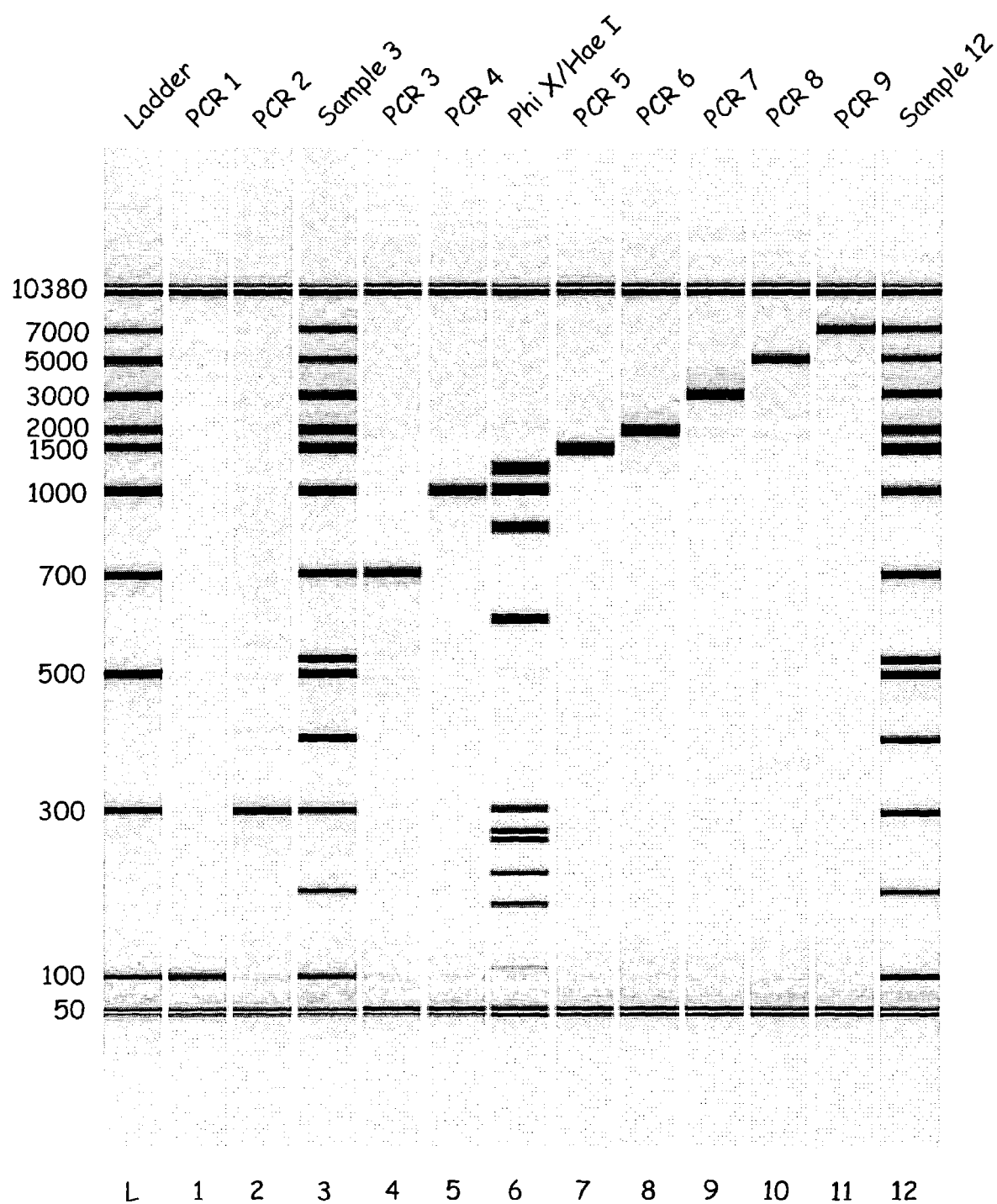
Figure 6A:
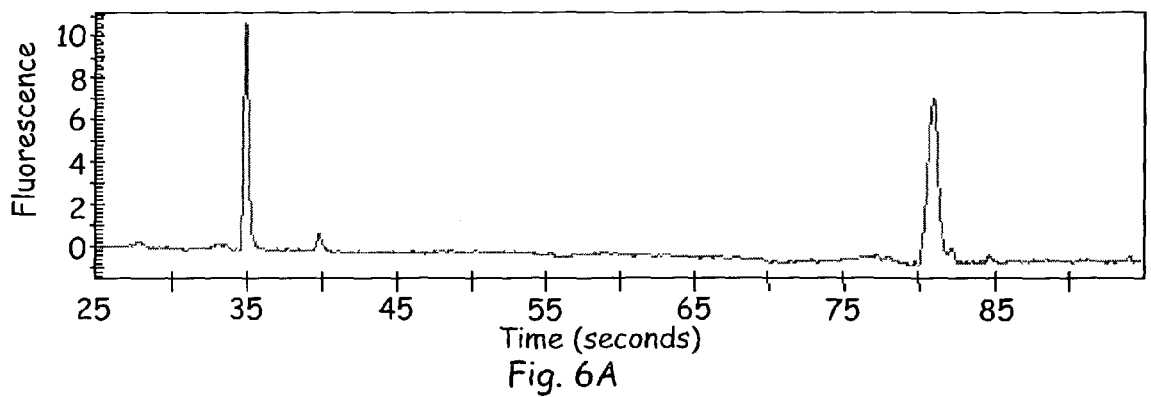
FIGS. 6A-D are plots of fluorescence versus time to identify collected fractions using the devices and methods of the present invention.
Figure 6B:
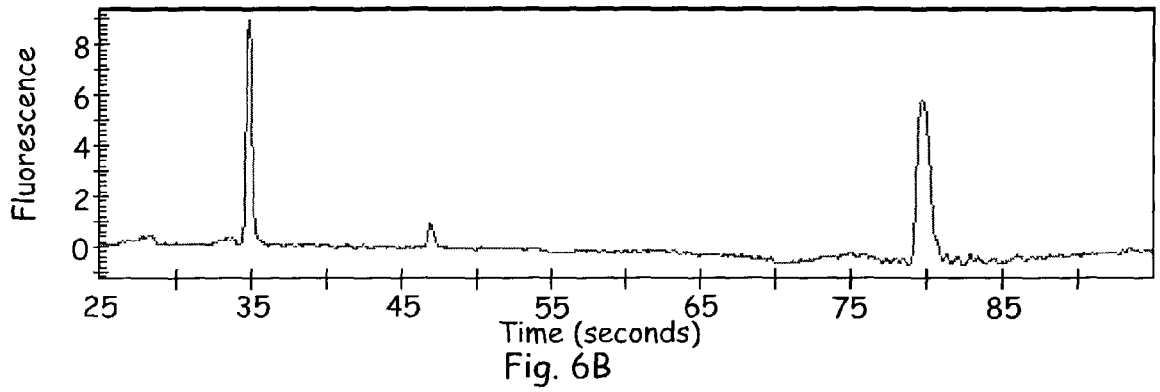
Figure 6C:
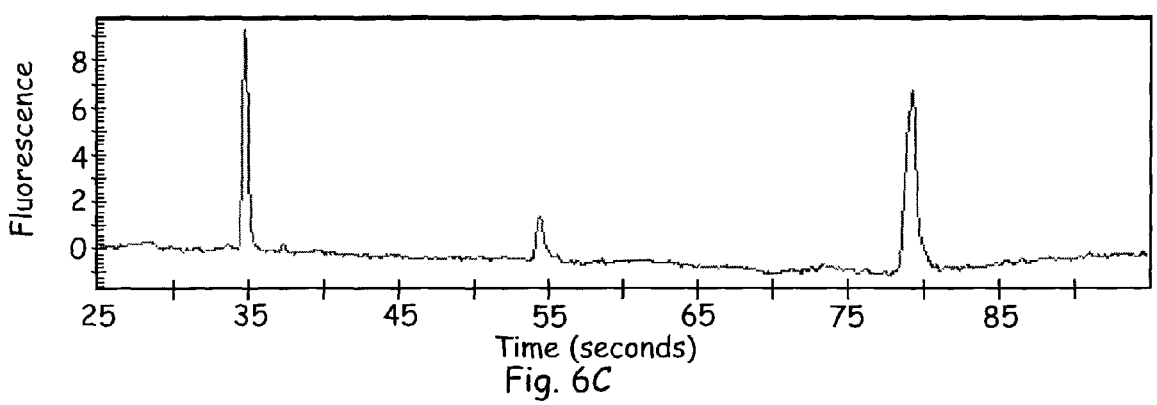
Figure 6D:
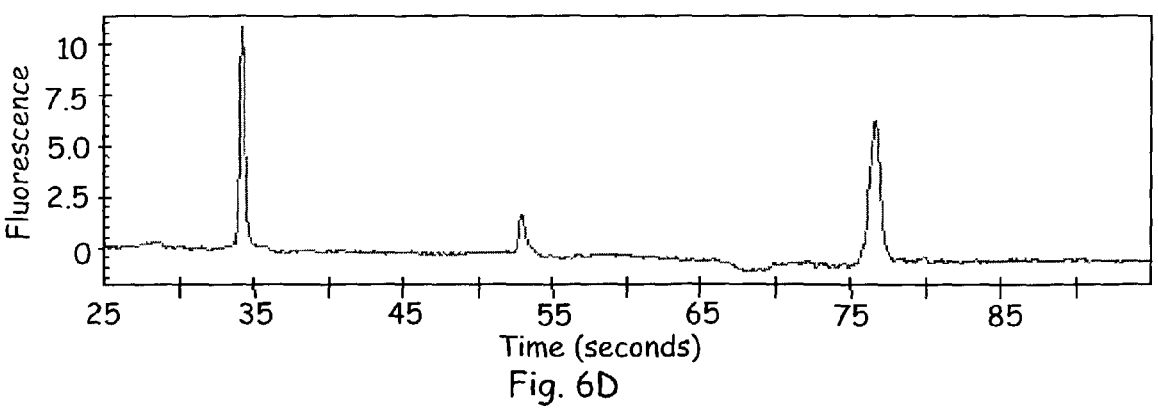

To minimize the impact of individual migration drift problems in the separation matrix when multiple samples are run through the device (which can render inaccurate proper selection and isolation of fragments of a particular size) as shown, for example, in FIG. 5A, the samples are typically co-run with flanking size markers of a known size (corresponding to the uppermost and lowermost bands of the sizing ladder) which allow accurate size calibration of every run. In such cases, the computer is typically programmed to identify the standards, e.g., by its location in the overall separation either first and/or last, and to determine the sizes (and/or molecular weights) of the unknown separated components in the sample by extrapolation or interpolation from the standard(s). A particularly useful computer software program for use in accordance with the separation methods of the present invention is described in commonly owned U.S. patent application Ser. No. 09/223,700 filed Dec. 29, 1998, the entire contents of which are incorporated by reference herein. A re-calibrated gel image taking into account run-to-run variability is shown in FIG. 5B, for example. However, because the computer-controlled size calibration cannot be performed until after the sample has been completely fractionated into its individual bands and the upper and lower flanking markers have flowed past the detector, a few approaches can be taken to ensure that the proper fragment of interest (e.g., fragment 293 in FIGS. 4C-D) is shunted into the collection conduit 216.

In one embodiment, a sample material is run completely through the separation conduit 214 and separated into its individual fragment bands without shunting the fragment of interest (e.g., fragment 293 in FIGS. 4C-D) into the collection conduit. Then, one (or more) additional samples from the same sample well(s) are run through the device a second time and separated into individual fragment bands as before. The computer can be programmed to identify a selected component of interest (based on a comparison to the sizing curve) as corresponding to a particular peak in the fluorescence versus time curve for each sample run through the device based on the recalibrated sizing data (as shown, for example, in FIG. 5B). Thus, for example, and with reference to FIG. 5B, if the user wishes to isolate a DNA fragment having a length of approximately 500 base pairs, such fragment corresponds to the sixth fluorescent peak (or band) in Sample 3 of FIG. 5B. When a second (or third or more) sample is run through the device, the computer can be programmed, for that particular sample, to instruct the operation of the controller 302 to direct fluid movement into the collection conduit when the sixth fluorescent peak is registered at the detection window 280 by the detector. Thus, one can ensure that a fragment of a given size is accurately shunted to the collection conduit. Additional sample material from the same sample well(s) can then be run through the device one or more additional times until a desired quantity of isolated sample fragments is collected in one or more of the sample collection wells. In this way, for example, sufficient DNA (or other sample material) product of a selected size required for a cloning operation can be collected in the device and prepared for on-chip cloning, if desired. Without calibrating the sample sizing data and running two or more samples through the device, for example, the computer likely would incorrectly shunt the fragment corresponding to the seventh band in FIG. 5A (which, as can be seen in FIG. 5B, is actually longer than 500 base pairs) into the collection conduit based on a one-time fluorescence versus time measurement and due to migration drift issues in the separation matrix.

Alternatively, in another embodiment of the invention, the length of the separation conduit 214 downstream from detection window 280 can be increased such that the sample fragments, separated by size, can be kept intact in the separation conduit after the flanking markers have flowed past the detection window. For example, the separation conduit can be configured to have a serpentine or other curved or extended configuration downstream from the detection window 280 to accommodate the full length of the sample, when separated by size into its individual fragments. The data of fluorescence versus time from the sample run through the separation conduit can be recalibrated by the computer as before (to compensate for band migration issues, e.g., band compression as shown in FIG. 5A, for example), and then the device operated such that the electric field in the separation conduit 214 is reversed causing the sample to move upstream in the opposite direction through the separation conduit. The sample, separated by size, will flow past the detector in the same band configuration, separated by size, as before. In this alternative embodiment, the collection conduit 216 would be located upstream from the detection window 280. Similar to the previous embodiment, the computer can then be programmed to instruct the operation of the controller to direct fluid movement into the collection conduit when the fluorescent peak corresponding to the correct size of the desired fragment (based on a comparison to the sizing curve) is registered at the detection window 280 by the detector. Thus, again, one can ensure that a fragment of a given size is accurately shunted to the collection conduit.

The device and methods of the present invention are widely applicable in the separation and isolation of a variety of macromolecular species. Such macromolecular species include without limitation, nucleic acids, proteins, peptides, carbohydrates, small molecules and the like. In particularly preferred aspects, the polymer compositions described herein are used in the electrophoretic separation and/or identification of nucleic acids in a sample. Such nucleic acids may include fragments or portions of genomic DNA, e.g., for genotyping, fragments or portions of mRNA, e.g., for gene expression analysis, or polymerization reaction products for verification of amplification processes. However, it will be appreciated that the present methods are suited to a wide variety of different separation based analyses, including chromatographic separations based upon the charge, hydrophobicity, size, relative affinity, etc. of the species to be separated.

Once the separation of the sample material is completed, and one or more fragments is isolated in the collection conduit using the methods of the present invention, one or more additional reservoirs such as reservoir 256 may be provided connected to the collection channel 216, e.g., via channel 257, to provide additional ligation or reaction agents to the collection channel 216. The agents supplied by reservoir 256 may be selected from a variety of different materials, such as a plasmid, a diluent, a detergent, a mass spectrometer MALDI matrix, a buffer solution (e.g., containing ATP for a ligation reaction), a protein affinity label, a ligation agent, or a combination of one or more of the above agents (for example to initiate a ligation or cloning reaction between a sample and a plasmid, for example). For example, for a cloning reaction, component reservoir 256 can contain one or more of a ligation enzyme (e.g., T4 ligase), a plasmid vector (e.g., a plasmid covalently linked to topoisomerase which then functions as a ligase such as a PCR II TOPO vector available commercially from Invitrogen (Carlsbad, Calif.)), sterile water, dNTP's, control template and primers, and M13 forward and reverse primers for sequencing or PCR screening, for example. Component reservoir 256 or another one or more reservoirs on the chip coupled to conduit 216 can also contain all of the reagents necessary for transformation, including, for example, competent E coli, beta-mercaptoethanol, SOC medium and supercoiled plasmid control pUC 18, for example.

The agents can be used for a variety of different reactions or analyses in the collection conduit (and/or in one of the collection conduits fluidly coupled thereto) including ligation reactions for cloning small to medium-sized strands of DNA into bacterial plasmids (e.g., E.coli cells), bacteriophages, and small animal viruses to allow the production of pure DNA in sufficient quantities to allow its chemical analysis, reactions to dissolve a separated protein or nucleic acid component in a suitable matrix for further analysis by a mass spectrometer using, for example, Matrix-Assisted Laser Desorption Ionization (MALDI), binding reactions to bind a labeling agent to one or more separated protein or nucleic acid components for further analysis, or other similar post-detection processes. The sample components or reaction mixture (in the case of a ligation reaction in the collection conduit, for example) can then be transported to one of the collection wells 262-270, for example, and then removed by the user for subsequent analysis (e.g., mass spectroscopy) or experimentation by optionally vortexing the device to homogenize the components therein to facilitate their removal from the collection well(s). The collection wells are preferably provided with a source of an appropriate lysis or wash buffer solution for cleansing the sample components for further analysis (in a mass spectroscopy instrument, for example).

In one preferred aspect of the present invention, for example, selected fragments of DNA can be incorporated into plasmids in the collection conduit 216 (or in one or more of the collection wells 262-270) by administering a plasmid into the collection conduit from reservoir 256. Thus, fragments of foreign DNA can be cloned in a linearized plasmid vector bearing compatible ends by the activity of Bacteriophage T4 DNA Ligase, which can also be provided via reagent reservoir 256. The enzyme will catalyze the formation of a phosphodiester bond between adjacent nucleotides if one nucleotide contains a 5'-phophate group and the other nucleotide contains a 3'-hydroxyl group. The plasmid DNA can be then be collected in one of the collection reservoirs 262-270, extracted, and introduced into modified bacteria (called competent cells) by the process of transformation.

The present invention is further illustrated with reference to the following non-limiting examples.

V. EXAMPLES

The principles of the present invention are illustrated in the following examples.

Example 1

Serial Separations-Based Analysis and Isolation of Fragments of Known Size

The device shown in FIG. 2 was used to perform a number of serial DNA separations and isolation of selected DNA fragments of known size, to verify the capability of the system to operate effectively in isolating fragments of a given size. All reagents were taken from a DNA 7500 LabChip® kit, commercially available from Agilent Technologies. The separation medium included a mixture of a sieving polymer solution and DNA intercalating dye. Four DNA fragments (150, 300, 500, and 950 bases) were dissolved in a $\frac{1}{100}$ dilution of DNA sample buffer in water (2 mM TAPS) with DNA flanking markers (40 pg/µl) and placed into each of the five sample loading reservoirs 240, 242, 244, 246, and 248, where each fragment was present at a concentration of 5 ng/µl. Because this Example was performed principally to validate the capability of the system to isolate fragments of known size/length, no DNA standard marker was used in this Example to generate a standard curve against which sample data was measured. All output collection wells 262, 264, 266, 268, and 270 were filled with 6 µl Pico buffer.

The microfluidic device was prepared by adding 9 μl of the separation medium to reservoir 254 (as shown in FIG. 2). The well was pressurized at 3 atm for 30 sec. 9 μl of separation medium was then added to wells 252, 256 and 258. Samples were added to wells 240, 242, 244, 246, and 248. The chip was then run on an Agilent 2100 Bioanalyzer commercially available from Agilent Technologies. Sample materials were then drawn into the sample loading channel, by applying an electric field of 900V to the sample well 260 for 90 seconds. A slight pinching current (0.5 μA in each channel portion) was applied for 2 seconds in separation channel 214 to avoid spreading of the sample plug at the intersection, and 900V was then applied along the length of the separation channel to move the DNA sample along the separation channel. Concurrently, a slight pull-back current (0.1 A in each direction) was applied to the portions of the injection channel 212. A sample from each sample well 240-248 was run through the separation conduit 214, detected at detection window 280, and then a fraction of each DNA fragment was shunted towards and collected in a separate collection well 262-270. A representative graph of fluorescence versus time from these runs is shown in FIG. 6, in which the second peak is the collected DNA fraction, while the first and third peaks are the lower and upper DNA markers, respectively. As shown, four out of the five DNA fragments (150 bases, 300 bases, 500 bases, and a repetition of 500 bases) were detected in the respective collection wells.

Example 2

Isolation and Cloning of a 750 bp PCR Product Into a PCR II Vector Via TOPO Cloning The following experiment was performed to illustrate the capability of the microfluidic device of FIG. 2 to separate and accurately isolate small quantities of DNA PCR fragments which were subsequently used in an off-chip cloning procedure, to verify that sufficient quantities of isolated PCR fragments could be collected using the methods and devices of the present invention and successfully used in cloning reactions.

Generation of a 750 bp DNA Product:

A control PCR fragment of 750 bp was synthesized using the components and procedure provided by the TOPO TA Cloning® kit from Invitrogen (Carlsbad, Calif.). After the PCR reaction, 1 μl of the 50 μl reaction mix was analyzed using a DNA 7500 LabChip® kit as described previously. The purified PCR product was found to have an average concentration of 7.6 ng/μl and the calculated MW is about 745 bp. The results of the analysis thus showed that the fragment size is as expected and the average concentration of the PCR product is at about 10 ng/μl in the reaction mixture.

The PCR product is further purified by ethanol precipitation after phenol extraction. The purified PCR product is resuspended in the same amount of TE buffer. The concentration of the purified product is usually slightly lower than the original mix. The 750 bp PCR product in both the original reaction mix and the purified form were subsequently used for a chip separation and isolation run (using, for example, the device of FIG. 2) and/or for TOPO cloning using a control which was not run through the microfluidic device (to estimate the threshold quantity of PCR fragment necessary for a successful cloning procedure).

Sample Cloning Procedure of a PCR Product:

TOPO TA Cloning® kits (K4500-01, K4600-01, available commercially from Invitrogen) were used for all the cloning procedures described herein. Briefly, a Taq polymerase-amplified PCR product is inserted into a plasmid by a reaction catalyzed by Topoisomerase I from Vaccinia. The TOPO reaction and the subsequent transformation reaction were carried out under conditions recommended by the manufacturer except that the control PCR product was manipulated before the TOPO reaction.

Typically the TOPO reaction mixture contains 1 μl control PCR product, 1 μl high salt concentrate, 3 μl water, and 1 μl PCR II TOPO vector. After 5 min reaction at room temperature, 2 μl of the reaction mixture is taken out and used for transformation with 50 μl chemically competent TOP 10 *E. coli* cells. Transformants are recovered in 250 μl SOC medium. In most experiments, 100 μl of the culture was plated on LB+amp+Kan+Xgal+IPTG for blue/white selection. Both blue and white colonies are counted. The white colonies are most likely recombinant clones with the PCR product as the insert.

Clone Analysis

The number of the white clones was used as an estimation of the cloning efficiency. The non-specific cloning background was estimated by counting the white colony numbers in the control TOPO reaction where sterile water was added in the place of any PCR products. In some experiments, further analysis of the clones was carried out by picking the white colonies, preparing plasmid DNA from the clones, and restriction digesting the plasmid to release the inserts. If the clone contains the PCR product insert that is not digested by the restriction enzyme EcoRI, it will show a fragment corresponding to the insert's size.

Results

PCR Product Quantitation

A microfluidic device as shown in FIG. 2 was used to isolate the purified PCR fragments, to verify the capability of the system to operate effectively in accurately isolating fragments of a given size. A total of 20 ng of the PCR product was loaded on each of the five sample wells 240, 242, 244, 246, and 248. The PCR fragment runs at about 50 sec on the device, and was collected into corresponding collection wells 262, 264, 266, 268, and 270 filled with 5 μl 2 mM TAPS buffer. The collected five fractions were then transferred to a freshly primed DNA pico chip for analysis. The first three wells of the DNA pico chip contains the fractions taken from the five collection wells 240-248 from the chip of FIG. 2, while the fourth well contains 2 mM TAPS buffer only. The first three samples all show a peak at about 65 sec while the peak is missing in the buffer only control in well #4. The analysis is not quantitative at the current assay format.

TOPO Cloning of the 750 bp PCR Product Taken From the Microfluidic Device

4 μl of each sample in the first four wells on the pico chip was then taken separately and used for the TOPO ligation reaction (4 μl sample mixed with 1 μl high salt solution and 1 μl TOPO PCRII vector). 250 μl of each of the SOC transformant culture was plated. The numbers of both white and blue colonies are listed in Table 1 below. The result shows that, as compared to the control buffer sample, the PCR fractions isolated with the microfluidic device consistently yielded significant numbers of white clones from the TOPO cloning reaction. All white colonies were further analyzed by EcoRI restriction digest. The number of white clones which were verified to actually contain the PCR product insert (based on a review of a gel image from an analysis of the restricted fragments taken from the white clones using a DNA 7500 LabChip® device) is also shown in Table 1.

TABLE 1

TOPO cloning of the 750 bp PCR product taken from the microfluidic device

| Sample source | Number of blue clones | Number of white clones | White clones that contain insert |
|---|---|---|---|
| Fraction 1 | 69 | 11 | 2 |
| Fraction 2 | 32 | 3 | 1 |
| Fraction 3 | 66 | 16 | 11 |
| Control sample | 65 | 0 | 0 |

TOPO Cloning of Serial Dilute 750 bp PCR Product

Another sample of the 750 bp PCR product was diluted in 2 mM TAPS, and then used in the TOPO reaction described above. When 10 fold serial diluted PCR product was tested, it was estimated that to see significant number to recombinant over the background, 10 to 100 pg PCR product is needed in the reaction mixture. Comparing the white clone number from the collected fragments taken from the device of FIG. 2 to the serial dilution experiment, it is estimated that there is about 10 pg 750 bp PCR product collected from each collection well 262-270.

Unless otherwise specified, all concentration values provided herein refer to the concentration of a given component as that component was added to a mixture or solution independent of any conversion, dissociation, reaction of that component to alter the component or transform that component into one or more different species once added to the mixture or solution. The method steps described herein are generally performable in any order unless an order is specifically provided or a required order is clear from the context of the recited steps. Typically, the recited orders of steps reflects one preferred order.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method of separating a sample material into a plurality of separated components and isolating one or more of said separated components comprising:

providing a microfluidic substrate including a separation conduit having a separation matrix disposed therein;

providing a detector in sensory communication with a first location along a length of the separation conduit for detecting said one or more separated components in the separation conduit;

providing a sample component collection conduit in said substrate in fluid communication with said separation conduit, said sample component collection conduit intersecting said separation conduit at a second location downstream from said first location, said sample component collection conduit in fluid communication with at least a first agent; providing a processor which is operably coupled to said detector and to a fluid direction system for controlling movement of sample components from said separation conduit into said sample component collection conduit based on information received from said detector, said processor including a computer that includes appropriate programming for receiving a signal from the detector that is indicative of a separated component passing the detector, transporting a first sample material through the separation conduit to separate the first sample material into a plurality of sample components;

detecting said plurality of sample components at said first location with said detector;

determining a retention time of the separated components in the separation conduit and determining a size of the separated components by comparing the retention time of the separated components to a retention time of components of a standard reference of known size for the sample material;

inputting instructions to the computer to direct the fluid direction system move a selected one or more of the separated components of interest from the separation conduit into the sample component collection conduit based on the determined size of the selected one or more sample components;

moving a selected one or more of said plurality of sample components from said separation conduit into the sample component collection conduit in response to instructions from the processor to the fluid direction system; and transporting an amount of the first agent into the sample component collection conduit to mix with the one or more sample components therein.

2. The method of claim 1, further comprising a sample loading conduit intersecting the separation conduit at a first fluid junction upstream of the first location, the loading conduit having a loading end and a waste end, the loading end being contacted with the source of the sample material, and further comprising applying a first pressure difference across the sample loading conduit to move the sample material into the loading end of the sample loading conduit and toward the waste end of the sample loading conduit.

3. The method of claim 2, wherein a negative pressure is applied to the waste end of the sample loading conduit to supply the first pressure difference across the sample loading conduit.

4. The method of claim 2 further comprising moving a portion of the sample material in the sample loading conduit through the first fluid junction and into the separation conduit.

5. The method of claim 4, wherein the sample material comprises one of a nucleic acid, a protein, or a carbohydrate.

6. The method of claim 4, wherein the step of moving the sample material from the sample loading conduit through the fluid junction and into the separation conduit comprises applying a voltage difference through the fluid junction to electrokinetically move the sample material from the sample loading conduit into the separation conduit.

7. The method of claim 1, wherein the step of separating the sample material comprises applying a voltage difference across the separation conduit, to electrophoretically separate the sample material into one or more sample components.

8. The method of claim 1, wherein the first agent is selected from a plasmid, a diluent, a detergent, a protein affinity label, or a ligation agent.

9. The method of claim 1, wherein the sample component collection conduit is in fluid communication with a source of at least a first ligation enzyme, and wherein the method further comprises transporting an amount of the first ligation enzyme into the sample component collection conduit to mix with the one or more sample components therein.

10. The method of claim 9 further comprising performing at least one ligation reaction between two or more sample components in the sample component collection conduit.

11. The method of claim 9 further comprising performing at least one ligation reaction between at least one sample component and a plasmid in the sample component collection conduit.

12. The method of claim 9, wherein the sample component collection conduit is in fluid communication with at least a first buffer solution containing ATP, and wherein the method further comprises transporting an amount of the first buffer solution into the sample component collection conduit to mix with the one or more sample components.

13. The method of claim 9, wherein the sample component collection conduit is in fluid communication with a source of a solution containing at least one plasmid, and wherein the method further comprises ligating said one or more sample components to said plasmid in at least a portion of the component collection conduit.

14. The method of claim 1, wherein the sample component collection conduit is in fluid communication with at least one component collection well, the method further comprising transporting said one or more sample components from said component collection conduit to said at least one collection well.

15. The method of claim 14 further comprising exposing the one or more sample components to a wash buffer solution in the at least one collection well.

16. The method of claim 15 further comprising vortexing the one or more components in the at least one collection well to homogenize the one or more components therein to facilitate their removal from the at least one collection well.

17. The method of claim 16 further comprising performing at least one analytical operation on the one or more sample component materials following their removal from the at least one collection well.

18. The method of claim 17 wherein said performing at least one analytical operation comprises performing a mass spectroscopy based analysis of the one or more sample components.

19. The method of claim 1 wherein the standard reference of known size is obtained by separating a standard sizing ladder.

20. The method of claim 19 wherein the separating a standard sizing ladder is performed prior to transporting the first sample material through the separation conduit to separate the first sample material into a plurality of first sample components.

21. The method of claim 20 wherein the reference standard sizing ladder is mixed with the sample material prior to said transporting step.

22. The method of claim 21 further comprising transporting two or more flanking size markers of a known size through the separation conduit simultaneously with said first sample material.

23. The method of claim 22 further comprising detecting said flanking size markers and separated components with the detector and comparing the known size of the flanking markers to the sizing ladder to obtain accurate sizing information of the separated components.

24. The method of claim 23 further comprising transporting the first sample material through the separation conduit at least two times prior to moving said selected one or more of said plurality of sample components from said separation conduit into the sample component collection conduit.

25. A method of separating a sample material into a plurality of separated components and isolating one or more of said separated components comprising:

providing a microfluidic substrate including a separation conduit having a separation matrix disposed therein;

providing a detector in sensory communication with a first location along a length of the separation conduit for detecting said one or more separated components in the separation conduit;

providing a sample component collection conduit in said substrate in fluid communication with said separation conduit, said sample component collection conduit intersecting said separation conduit at a second location downstream from said first location;

providing a user-programmable processor which is operably coupled to said detector and to a fluid direction system, the processor including appropriate programming for receiving a signal from the detector that is indicative of a separated component passing the detector, transporting a first sample material through the separation conduit to separate the first sample material into a plurality of first sample components;

detecting said plurality of first sample components at said first location with said detector;

determining a retention time of the separated components in the separation conduit, and determining a size of the separated components by comparing the retention time of the separated components to a retention time of components of a standard reference of known size for the sample material;

inputting instructions to the processor to direct the fluid direction system to move a selected one or more of the separated components of interest from the separation conduit into the sample component collection conduit based on the determined size of the selected one or more sample components; and moving said selected one or more of said plurality of first sample components from said separation conduit into the sample component collection conduit in response to said instructions from the processor to the fluid direction system.

26. The method of claim 25 wherein the standard reference of known size is obtained by separating a standard sizing ladder.

27. The method of claim 26 wherein the separating a standard sizing ladder is performed prior to transporting the first sample material through the separation conduit to separate the first sample material into a plurality of first sample components.

28. The method of claim 26 wherein the reference standard sizing ladder is mixed with the sample material prior to said transporting step.

29. The method of claim 25 further comprising transporting two or more flanking size markers of a known size through the separation conduit simultaneously with said first sample material.

30. The method of claim 29 further comprising detecting said flanking size markers and separated components with the detector and comparing the known size of the flanking markers to the sizing ladder to obtain accurate sizing information of the separated components.

31. The method of claim 30 further comprising transporting the first sample material through the separation conduit at least two times prior to moving said selected one or more of said plurality of sample components from said separation conduit into the sample component collection conduit.

* * * * *